(12) United States Patent
Weng et al.

(10) Patent No.: US 9,203,112 B2
(45) Date of Patent: Dec. 1, 2015

(54) REDOX SHUTTLES HAVING AN AROMATIC RING FUSED TO A 1,1,4,4-TETRASUBSTITUTED CYCLOHEXANE RING

(75) Inventors: Wei Weng, Woodridge, IL (US); Zhengcheng Zhang, Naperville, IL (US); Khalil Amine, Oakbrook, IL (US)

(73) Assignee: UCHICAGO ARGONNE, LLC, Chicago, IL (US)

( * ) Notice: Subject to any disclaimer, the term of this patent is extended or adjusted under 35 U.S.C. 154(b) by 767 days.

(21) Appl. No.: 13/457,239

(22) Filed: Apr. 26, 2012

(65) Prior Publication Data
US 2013/0288137 A1 Oct. 31, 2013

(51) Int. Cl.
| | |
|---|---|
| *H01M 10/0567* | (2010.01) |
| *H01M 6/16* | (2006.01) |
| *C07C 43/21* | (2006.01) |
| *C07C 43/225* | (2006.01) |

(52) U.S. Cl.
CPC .......... *H01M 10/0567* (2013.01); *C07C 43/21* (2013.01); *C07C 43/225* (2013.01); *H01M 6/168* (2013.01); *H01M 2300/0025* (2013.01); *Y02E 60/122* (2013.01)

(58) Field of Classification Search
CPC ............ H01M 10/0567; H01M 6/168; H01M 2300/0025; Y02E 60/122
See application file for complete search history.

(56) References Cited

U.S. PATENT DOCUMENTS

| | | |
|---|---|---|
| 6,203,944 B1 | 3/2001 | Turner et al. |
| 6,255,017 B1 | 7/2001 | Turner |
| 6,436,578 B2 | 8/2002 | Turner et al. |
| 6,664,004 B2 | 12/2003 | Krause et al. |
| 6,699,336 B2 | 3/2004 | Turner et al. |
| 7,851,092 B2 | 12/2010 | Amine et al. |
| 8,101,302 B2 | 1/2012 | Lamanna et al. |
| 2003/0211390 A1 | 11/2003 | Dahn et al. |
| 2004/0131936 A1 | 7/2004 | Turner et al. |
| 2005/0019670 A1 | 1/2005 | Amine et al. |
| 2005/0031957 A1 | 2/2005 | Christensen et al. |
| 2006/0046144 A1 | 3/2006 | Obrovac |
| 2007/0072085 A1 | 3/2007 | Chen et al. |
| 2007/0178370 A1 | 8/2007 | Amine et al. |
| 2007/0235259 A1 | 10/2007 | Tolliver et al. |
| 2010/0040954 A1 | 2/2010 | Amine et al. |
| 2011/0294017 A1 | 12/2011 | Weng et al. |
| 2011/0294018 A1 | 12/2011 | Zhang et al. |

OTHER PUBLICATIONS

U.S. Appl. No. 61/529,413, filed Aug. 31, 2011, Zhang et al.
Buhrmester et al., "Studies of Aromatic Redox Shuttle Additives for LiFePO$_4$-Based Li-Ion Cells", Journal of the Electrochemical Society, vol. 152, Issue 12, 2005, pp. A2390-A2399.
Chen et al., "Bifunctional electrolyte additive for lithium-ion batteries", Electrochem. Commun., 9, 2007, pp. 703-707.
Moshurchak, L.M. et al., "High-Potential Redox Shuttle for Use in Lithium-Ion Batteries", Journal of the Electrochemical Society, 156, (4), (2009), pp. A309-A312.

*Primary Examiner* — Laura Weiner
(74) *Attorney, Agent, or Firm* — Foley & Lardner LLP

(57) ABSTRACT

An electrolyte includes an alkali metal salt; an aprotic solvent; and a redox shuttle additive including an aromatic compound having at least one aromatic ring fused with at least one non-aromatic ring, the aromatic ring having two or more oxygen or phosphorus-containing substituents.

18 Claims, 7 Drawing Sheets

REDOX SHUTTLES HAVING AN AROMATIC RING FUSED TO A 1,1,4,4-TETRASUBSTITUTED CYCLOHEXANE RING

GOVERNMENT RIGHTS

This invention was made with Government support under Contract No. DE-AC02-06CH11357 awarded by the Department of Energy. The Government has certain rights in this invention.

FIELD

The present technology relates generally to lithium rechargeable batteries, and more particularly to high voltage reduction-oxidation (e.g. redox) shuttles for use in electrochemical cells and batteries.

SUMMARY

In one aspect, an electrolyte is provided including an alkali metal salt; an aprotic solvent; and a redox shuttle additive including an aromatic compound having at least one aromatic ring fused with at least one non-aromatic ring, the aromatic ring having two or more oxygen or phosphorus-containing substituents. In some embodiments, the redox shuttle includes a compound represented by Formula I, II, III, or IV:

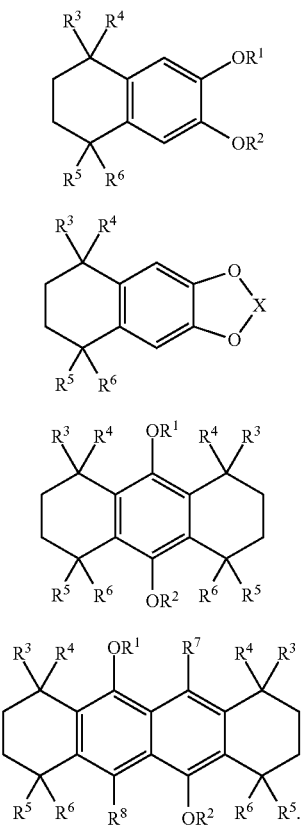

In Formulas I, II, III, an IV, $R^1$ and $R^2$ are independently alkyl, $P(O)R^9R^{10}$, $P(O)(OR^9)(OR^{10})$, or $P(OR^9)(OR^{10})$; $R^3$, $R^4$, $R^5$ and $R^6$ are independently F or alkyl; $R^7$, and $R^8$ are independently H, alkyl, or alkoxy; $R^9$ and $R^{10}$ are independently alkyl; X is alkylene, $BR^{11}$, or $P(O)OR^{12}$; $R^{11}$ is alkyl or aryl; and $R^{12}$ is alkyl. In some embodiments, the $R^1$ and $R^2$ are independently $C_1$-$C_8$ alkyl, $P(O)R^9R^{10}$, $P(O)(OR^9)(OR^{10})$, or $P(OR^9)(OR^{10})$; $R^3$, $R^4$, $R^5$ and $R^6$ are independently F, or $C_1$-$C_2$ alkyl; $R^7$, and $R^8$ are independently H, $C_1$-$C_8$ alkyl, or $C_1$-$C_8$ alkoxy; $R^9$ and $R^{10}$ are independently $C_1$-$C_8$ alkyl; X is $C_1$-$C_4$ alkylene, $BR^{11}$, or $P(O)OR^{12}$; $R^{11}$ is $C_1$-$C_8$ alkyl or $C_6$-$C_{12}$ aryl; and $R^{12}$ is $C_1$-$C_8$ alkyl. In other embodiments, $R^1$ and $R^2$ are independently $C_1$-$C_8$ alkyl or $C_1$-$C_8$ fluoroalkyl, $P(O)R^9R^{10}$, $P(O)(OR^9)(OR^{10})$, or $P(OR^9)(OR^{10})$; $R^3$, $R^4$, $R^5$ and $R^6$ are independently F, $C_1$-$C_2$ alkyl, or $C_1$-$C_2$ fluoroalkyl; $R^7$, and $R^8$ are independently H, $C_1$-$C_8$ alkyl, $C_1$-$C_8$ fluoroalkyl, $C_1$-$C_8$ alkoxy, or $C_1$-$C_8$ fluoroalkoxy; $R^9$ and $R^{10}$ are independently $C_1$-$C_8$ alkyl or $C_1$-$C_8$ fluoroalkyl; X is $C_1$-$C_4$ alkylene, $BR^{11}$, or $P(O)OR^{12}$; $R^{11}$ is $C_1$-$C_8$ alkyl, $C_1$-$C_8$ fluoroalkyl, or substituted or unsubstituted phenyl; and $R^{12}$ is $C_1$-$C_8$ alkyl or $C_1$-$C_8$ fluoroalkyl.

In one embodiment, the redox shuttle includes a compound represented by Formula I and $R^1$ and $R^2$ are $C_1$-$C_8$ alkyl or $C_1$-$C_8$ fluoroalkyl, $P(O)R^9R^{10}$, $P(O)(OR^9)(OR^{10})$, or $P(OR^9)(OR^{10})$; $R^3$, $R^4$, $R^5$ and $R^6$ are independently F, $C_1$-$C_2$ alkyl, $C_1$-$C_2$ fluoroalkyl; and $R^9$ and $R^{10}$ are independently $C_1$-$C_8$ alkyl. In one embodiment, $R^1$ and $R^2$ are independently $CH_3$, $CH_2CH_3$, $CH_2CH_2CH_3$, $CH_2CH_2CH_2CH_3$, $CH(CH_3)_2$, $CH_2CH(CH_3)_2$, $CH_2CH_2OCH_3$, $CH_2CH_2OCH_2CH_2OCH_3$, $CH_2F$, $CH_2CF_3$, $CH_2CF_2M$, $CH_2CF_2CF_2CF_3$, $CH_2CF_2CF_2H$, $CH_2CF_2OCF_2H$, $CH_2CF_2OCF_2CF_2OCF_2H$; $P(O)(OCH_3)_2$, $P(O)(OCH_2CH_3)_2$, $P(O)(CH_3)_2$, or $P(O)(CH_2CH_3)_2$.

In one embodiment, the redox shuttle includes a compound represented by Formula II and $R^1$ and $R^2$ are $C_1$-$C_8$ alkyl or $C_1$-$C_8$ fluoroalkyl, $P(O)R^9R^{10}$, $P(O)(OR^9)(OR^{10})$, or $P(OR^9)(OR^{10})$; $R^3$, $R^4$, $R^5$ and $R^6$ are independently F, $C_1$-$C_2$ alkyl, $C_1$-$C_2$ fluoroalkyl; and $R^9$ and $R^{10}$ are independently $C_1$-$C_8$ alkyl; and X is $C_1$-$C_4$ alkylene, $BR^{11}$, or $P(O)OR^{12}$; $R^{11}$ is $C_1$-$C_8$ alkyl, $C_1$-$C_8$ fluoroalkyl, or substituted or unsubstituted phenyl; and $R^{12}$ is $C_1$-$C_8$ alkyl or $C_1$-$C_8$ fluoroalkyl. In one embodiment, $R^1$ and $R^2$ are independently $CH_3$, $CH_2CH_3$, $CH_2CH_2CH_3$, $CH_2CH_2CH_2CH_3$, $CH(CH_3)_2$, $CH_2CH(CH_3)_2$, $CH_2CH_2OCH_3$, $CH_2CH_2OCH_2CH_2OCH_3$, $CH_2CF_3$, $CH_2CF_2CF_3$, $CH_2CF_2CF_2CF_3$, $CH_2CF_2CF_2H$, $CH_2CF_2OCF_2H$, $CH_2CF_2OCF_2CF_2OCF_2H$; $P(O)(CH_3)_2$, $P(O)(CH_2CH_3)_2$, $P(O)(CH_3)_2$, or $P(O)(CH_2CH_3)_2$. In any of the embodiments, X may be BPh, $CH_2$, $CH_2CH_2CH_2CH_2CH_2$, $CH_2CH_2CH_2CH_2$, $P(O)OCH_3$, or $P(O)OCH_2CH_3$.

In one embodiment, the redox shuttle includes

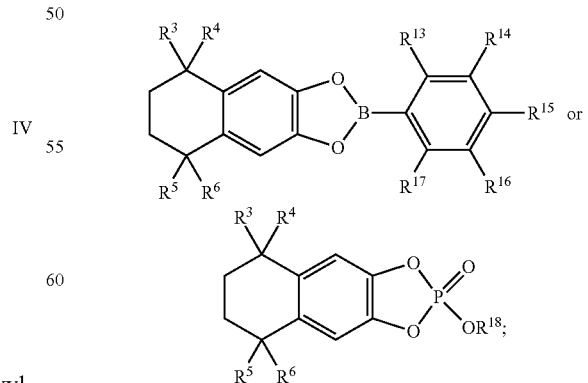

wherein $R^3$, $R^4$, $R^5$ and $R^6$ are independently F or alkyl; and $R^{13}$, $R^{14}$, $R^{15}$, $R^{16}$, $R^{17}$ and $R^{18}$ are independently H, F, Cl, Br, or alkyl. In some embodiments, $R^3$, $R^4$, $R^5$ and $R^6$ are $CH_3$ or $CH_2CH_3$; and $R^{13}$, $R^{14}$, $R^{15}$, $R^{16}$, $R^{17}$, and $R^{18}$ are independently H, F, Cl, Br, $CH_3$, $CH_2CH_3$, $CH_2CH_2CH_3$, $CH(CH_3)_2CH_2$, $CF_3$, $CH_2CF_3$, or $CH_2CF_2CF_3$.

In one embodiment, the redox shuttle includes a compound of Formula IV:

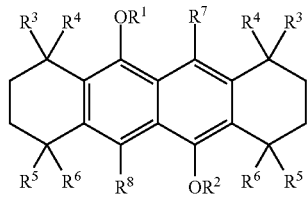

IV wherein: $R^3$, $R^4$, $R^5$ and $R^6$ are independently F or alkyl; and $R^1$ and $R^2$ are independently $CH_3$, $CH_2CH_3$, $CH_2CH_2CH_3$, $CH_2CH_2CH_2CH_3$, $CH(CH_3)_2$, $CH_2CH(CH_3)_2$, $CH_2CH_2OCH_3$, $CH_2CH_2OCH_2CH_2OCH_3$, $CH_2F$, $CH_2CF_3$, $CH_2CF_2CF_3$, $CH_2CF_2CF_2CF_3$, $CH_2CF_2CF_2H$, or $CH_2CF_2OCF_2H$, or $CH_2CF_2OCF_2CF_2OCF_2H$; and $R^7$ and $R^8$ are independently H, methyl, ethyl, methoxy, ethoxy, or trifluoromethoxy.

In any of the above embodiments, the redox shuttle is present in the electrolyte from about 0.05 wt % to about 50 wt %, based upon the weight of the redox shuttle and the aprotic solvent. In any of the above embodiments, the alkali metal salt is a lithium salt. In any of the above embodiments, the lithium salt includes LiBr, LiI, LiSCN, $LiBF_4$, $LiAlF_4$, $LiPF_6$, $LiAsF_6$, $LiClO_4$, $Li_2SO_4$, $LiB(Ph)_4$, $LiAlO_2$, $Li[N(FSO_2)_2]$, $Li[SO_3CH_3]$, $Li[BF_3(C_2F_5)]$, $Li[PF_3(CF_2CF_3)_3]$, $Li[B(C_2O_4)_2]$, $Li[B(C_2O_4)F_2]$, $Li[PF_4(C_2O_4)]$, $Li[PF_2(C_2O_4)_2]$, $Li[CF_3CO_2]$, $Li[C_2F_5CO_2]$, $Li[N(CF_3SO_2)_2]$, $Li[C(SO_2CF_3)_3]$, $Li[N(C_2F_5SO_2)_2]$, $Li[CF_3SO_3]$, $Li_2B_{12}X_{12-n}H_n$, $Li_2B_{10}X^2_{10-n}H_n$, $Li_2S_{x'''}$, $(LiS_{x''}R^1)_y$, $(LiSe_{x''}R^1)_y$, and lithium alkyl fluorophosphates; where $X^2$ is a halogen, n is an integer from 0 to 12, n' is an integer from 0 to 10, x'' is an integer from 1 to 20, y is an integer from 1 to 3, and $R^1$ is H, alkyl, alkenyl, aryl, ether, F, $CF_3$, $COCF_3$, $SO_2CF_3$, or $SO_2F$. In any of the above embodiments, the lithium salt may include $Li[(C_2O_4)_2B]$, $Li(C_2O_4)BF_2$, $LiClO_4$, $LiBF_4$, $LiAsF_6$, $LiPF_6$, $LiCF_3SO_3$, $Li(CF_3SO_2)_2N$, $Li(CF_3SO_2)_3C$, $LiN(SO_2C_2F_5)_2$, or a lithium alkyl fluorophosphate.

In any of the above embodiments, the polar aprotic solvent includes ethylene carbonate, propylene carbonate, dimethyl carbonate, diethyl carbonate, ethyl methyl carbonate, dimethyl ether, or gamma butyrolactone.

In another aspect, an electrochemical device is provided including any of the above electrolytes.

In another aspect, a lithium ion battery is provided including a cathode, an anode, and any of the above electrolytes.

The foregoing summary is illustrative only and is not intended to be in any way limiting. In addition to the illustrative aspects, embodiments and features described above, further aspects, embodiments and features will become apparent by reference to the following drawings and the detailed description.

DETAILED DESCRIPTION

Figure 1:
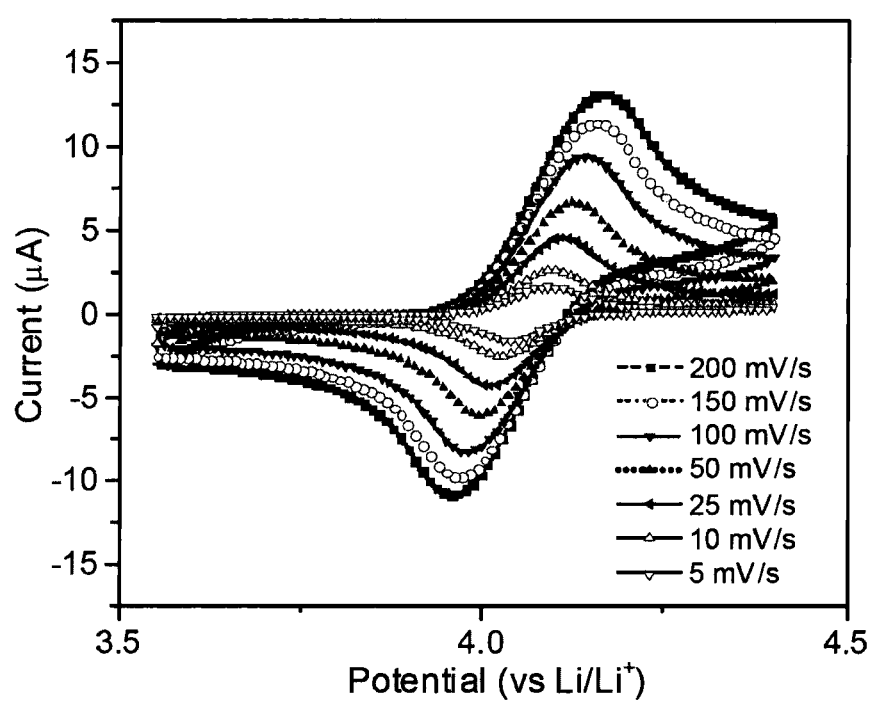
FIG. 1 is a cyclic voltammogram (positive scan) of 1,2,3,4-tetrahydro-6,7-dimethoxy-1,1,4,4-tetramethylnaphthalene (5 mM) in 1.2 M $LiPF_6$ in EC/EMC (3:7 wt ratio) using a three electrode system (Pt working Electrode, Li counter electrode and Li reference electrode) at different scan rates, according to the examples.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The technology is described herein using several definitions, as set forth throughout the specification.

The use of the terms "a" and "an" and "the" and similar referents in the context of describing the elements (especially in the context of the following claims) are to be construed to cover both the singular and the plural, unless otherwise indicated herein or clearly contradicted by context.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Alkyl groups include straight chain and branched alkyl groups having from 1 to about 20 carbon atoms, and typically from 1 to 12 carbons or, in some embodiments, from 1 to 8 carbon atoms. As employed herein, "alkyl groups" include cycloalkyl groups as defined below. Examples of straight chain alkyl groups include methyl, ethyl, n-propyl, n-butyl, n-pentyl, n-hexyl, n-heptyl, and n-octyl groups. Examples of branched alkyl groups include, but are not limited to, isopropyl, sec-butyl, t-butyl, neopentyl, and isopentyl groups. Representative substituted alkyl groups may be substituted one or more times with, for example, amino, thio, hydroxy, cyano, alkoxy, and/or halo groups such as F, Cl, Br, and I groups. As used herein the term haloalkyl is an alkyl group having one or more halo groups. In some embodiments, haloalkyl refers to a an alkyl group having from one halo substituent to being a pehaloalkyl group. Alkylene groups are divalent alkyl groups, where there are two points of attachment. Illustrative examples of alkylene groups include, but are not limited to $CH_2$ (methylene), $CH_2CH_2$ (ethylene), $CH_2CH_2CH_2$ (propylene), $C(CH_3)_2$ (isopropylene), etc.

Fluoroalkyl groups include straight chain and branched alkyl groups having from 1 to about 20 carbon atoms, and typically from 1 to 12 carbons or, in some embodiments, from 1 to 8 carbon atoms, where at least one hydrogen atom on the alkyl group is replaced by a fluorine atom. Such fluoroalkyl groups may be monofluorinated groups, up to, and including, perfluorinated groups. As employed herein, "fluoroalkyl groups" include fluorinated cycloalkyl groups. Illustrative examples include fluorinated methyl groups such as $CH_2F$, $CHF_2$, and $CF_3$. Other fluorinated alkyl groups include, but are not limited to, those where the underlying alkyl group is as defined above.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups may be mono-substituted or substituted more than once, such as, but not limited to: 2,2-; 2,3-; 2,4-; 2,5-; or 2,6-disubstituted cyclohexyl groups or mono-, di-, or tri-substituted norbornyl or cycloheptyl groups, which may be substituted with, for example, alkyl, alkoxy, amino, thio, hydroxy, cyano, and/or halo groups.

Aryl groups are cyclic aromatic hydrocarbons of 6 to 14 carbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain from 6 to 12 or even 6 to 10 carbon atoms in the ring portions of the groups. In some embodiments, the aryl groups are phenyl or naphthyl. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halogen groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above. Arylene groups are divalent aryl groups, where there are two points of attachment. Illustrative examples of arylene groups include, but are not limited to $C_6H_4$ (phenylene—all isomers), $C_6H_3CH_3$ (tolylene—all isomers), and $C_6H_4CH_2$.

Alkoxy groups are hydroxyl groups (—OH) in which the bond to the hydrogen atom is replaced by a bond to a carbon atom of an alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Representative substituted alkoxy groups may be substituted one or more times with substituents such as those listed above.

The term "hydroxyl" refers to —OH groups.

"Substituted" refers to a chemical group as described herein that further includes one or more substituents, such as lower alkyl (including substituted lower alkyl such as haloalkyl, hydroxyalkyl, aminoalkyl), aryl (including substituted aryl), acyl, halogen, hydroxy, amino, alkoxy, alkylamino, acylamino, thioamido, acyloxy, aryloxy, aryloxyalkyl, carboxy, thiol, sulfide, sulfonyl, oxo, both saturated and unsaturated cyclic hydrocarbons (e.g., cycloalkyl, cycloalkenyl), cycloheteroalkyls and the like. These groups may be attached to any carbon or substituent of the alkyl, alkenyl, alkynyl, aryl, cycloheteroalkyl, alkylene, alkenylene, alkynylene, arylene, hetero moieties. Additionally, the substituents may be pendent from, or integral to, the carbon chain itself.

A new class of redox shuttles is described herein which can withstand overcharging conditions of greater than 4V. The incorporation of such shuttles into electrolytes or into lithium ion batteries can improve their performance. For example, the use of such shuttles in batteries makes them safer to use, and allows for further reductions in their size and volume. Redox shuttles are those materials that may be added to an electrochemical system at a low concentrations, but which materials are reversibly oxidized and reduced at a defined potential slightly higher than the end-of-charge potential of the positive electrode. During recharging, when the maximum charge of the positive electrode is reached, either through the maximum capacity being attained or the charging current is such that the charging rate exceeds that which the electrode can handle, the redox shuttle becomes oxidized to absorb the excess charge without deleteriously impacting the electrode or bulk electrolyte in the battery. This mechanism can protect the cell from overcharge by locking the potential of the positive electrode at the oxidation potential of the shuttle molecules.

Thus, in a first aspect an electrolyte is provided. The electrolytes include an alkali metal salt; an aprotic solvent; and a redox shuttle. The redox shuttles described herein are aromatic compounds having at least one aromatic ring fused with at least one non-aromatic ring, and the aromatic ring has two or more oxygen or phosphorus-containing substituents, preferably where the oxygen is attached to the aromatic ring, or where the phosphorus is attached to the aromatic ring through an oxygen atom. The redox shuttles have relative high redox potentials to be used as overcharge protectants. For example, the redox shuttles may exhibit a redox potential of about 3.5 V to about 5.3V, in the electrolytes.

The redox shuttles may include a compound as represented by Formula I, II, III, or IV:

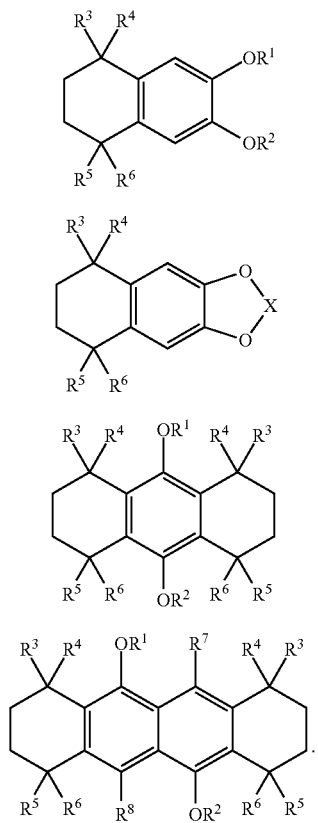

In Formula I, II, III, and IV, $R^1$ and $R^2$ are independently alkyl, $P(O)R^9R^{10}$, $P(O)(OR^9)(OR^{10})$, or $P(OR^9)(OR^{10})$; $R^3$, $R^4$, $R^5$ and $R^6$ are independently F or alkyl; $R^7$, and $R^8$ are independently H, alkyl, or alkoxy; $R^9$ and $R^{10}$ are independently alkyl; X is alkylene, $BR^{11}$, or $P(O)OR^{12}$; $R^{11}$ is alkyl or aryl; and $R^{12}$ is alkyl. In one embodiment of Formula I, II, III, and IV, $R^1$ and $R^2$ independently alkyl. In one embodiment, the compound is represented by Formula I. In another embodiment, the compound is represented by Formula II. In another embodiment, the compound is represented by Formula III. In another embodiment, the compound is represented by Formula IV.

In any of the above embodiments, $R^1$ and $R^2$ are independently $C_1$-$C_8$ alkyl, $P(O)R^9R^{10}$, $P(O)(OR^9)(OR^{10})$, or $P(OR^9)(OR^{10})$; $R^3$, $R^4$, $R^5$ and $R^6$ are independently F or $C_1$-$C_2$ alkyl; $R^7$, and $R^8$ are independently H, $C_1$-$C_8$ alkyl, or $C_1$-$C_8$ alkoxy; $R^9$ and $R^{10}$ are independently $C_1$-$C_8$ alkyl; X is $C_1$-$C_4$ alkylene, $BR^{11}$, or $P(O)OR^{12}$; $R^{11}$ is $C_1$-$C_8$ alkyl or $C_6$-$C_{12}$ aryl; and $R^{12}$ is $C_1$-$C_8$ alkyl. In any of the above embodiments, $R^1$ and $R^2$ are independently $C_1$-$C_8$ alkyl or $C_1$-$C_8$ fluoroalkyl, $P(O)R^9R^{10}$, $P(O)(OR^9)(OR^{10})$, or $P(OR^9)(OR^{10})$; $R^3$, $R^4$, $R^5$ and $R^6$ are independently F, $C_1$-$C_2$ alkyl, or $C_1$-$C_2$ fluoroalkyl $R^7$, and $R^8$ are independently H, $C_1$-$C_8$ alkyl, $C_1$-$C_8$ fluoroalkyl, $C_1$-$C_8$ alkoxy, or $C_1$-$C_8$ fluoroalkoxy; $R^9$ and $R^{10}$ are independently $C_1$-$C_8$ alkyl or $C_1$-$C_8$ fluoroalkyl; X is $C_1$-$C_4$ alkylene, $BR^{11}$, or $P(O)OR^{12}$; $R^{11}$ is $C_1$-$C_8$ alkyl, $C_1$-$C_8$ fluoroalkyl, or substituted or unsubstituted phenyl; and $R^{12}$ is $C_1$-$C_8$ alkyl or $C_1$-$C_8$ fluoroalkyl.

According to one embodiment where the redox shuttle includes a compound represented by Formula I, $R^1$ and $R^2$ are $C_1$-$C_8$ alkyl or $C_1$-$C_8$ fluoroalkyl, $P(O)R^9R^{10}$, $P(O)(OR^9)(OR^{10})$, or $P(OR^9)(OR^{10})$; $R^3$, $R^4$, $R^5$ and $R^6$ are independently F, $C_1$-$C_2$ alkyl, $C_1$-$C_2$ fluoroalkyl; and $R^9$ and $R^{10}$ are independently $C_1$-$C_8$ alkyl. According to one embodiment where the redox shuttle includes a compound represented by Formula II, $R^1$ and $R^2$ are $C_1$-$C_8$ alkyl or $C_1$-$C_8$ fluoroalkyl, $P(O)R^9R^{10}$, $P(O)(OR^9)(OR^{10})$, or $P(OR^9)(OR^{10})$; $R^3$, $R^4$, $R^5$ and $R^6$ are independently F, $C_1$-$C_2$ alkyl, $C_1$-$C_2$ fluoroalkyl; and $R^9$ and $R^{10}$ are independently $C_1$-$C_8$ alkyl; and X is $C_1$-$C_4$ alkylene, $BR^{11}$, or $P(O)OR^{12}$; $R^{11}$ is $C_1$-$C_8$ alkyl, $C_1$-$C_8$ fluoroalkyl, or substituted or unsubstituted phenyl; and $R^{12}$ is $C_1$-$C_8$ alkyl or $C_1$-$C_8$ fluoroalkyl.

In any of the above embodiments, $R^1$ and $R^2$ may be independently $CH_3$, $CH_2CH_3$, $CH_2CH_2CH_3$, $CH_2CH_2CH_2CH_3$, $CH(CH_3)_2$, $CH_2CH(CH_3)_2$, $CH_2CH_2OCH_3$, $CH_2CH_2OCH_2CH_2OCH_3$, $CH_2F$, $CH_2CF_3$, $CH_2CF_2CF_3$, $CH_2CF_2CF_2CF_3$, $CH_2CF_2CF_2H$, $CH_2CF_2OCF_2H$, $CH_2CF_2OCF_2CF_2OCF_2H$; $P(O)(OCH_3)_2$, $P(O)(OCH_2CH_3)_2$, $P(O)(CH_3)_2$, or $P(O)(CH_2CH_3)_2$. In any of the above embodiments, X may be BPh, $CH_2$, $CH_2CH_2$, $CH_2C_2H_2$, $CH_2CH_2CH_2CH_2$, $P(O)OCH_3$, or $P(O)OCH_2CH_3$.

By way of illustration only, and not intending to be limiting, the redox shuttles of Formula I and II may include compounds such as:

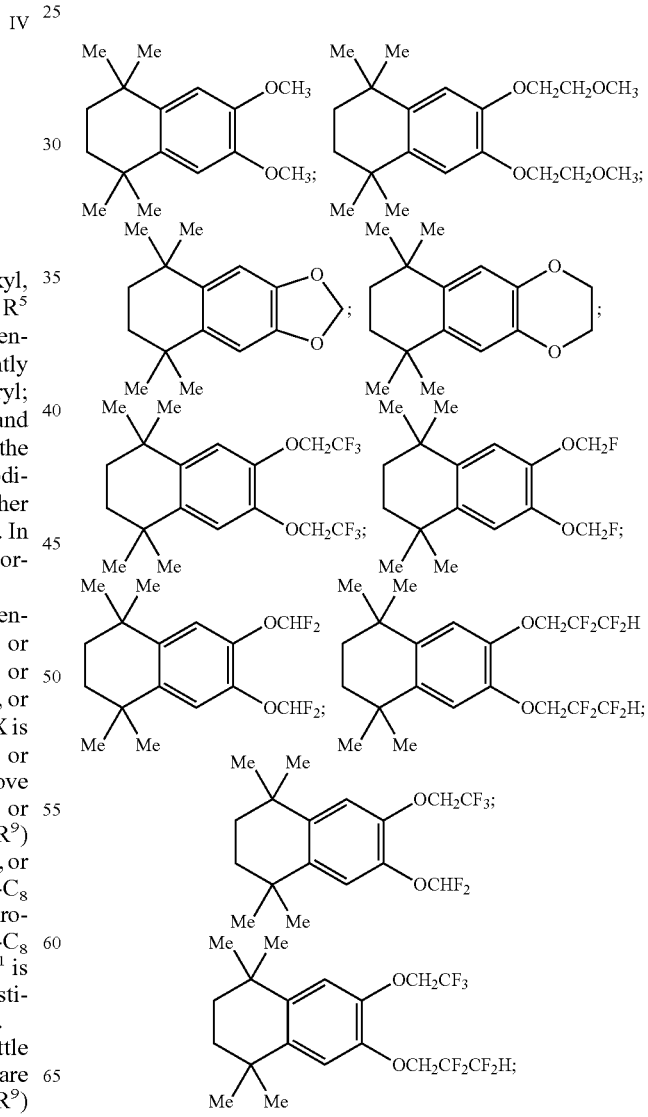

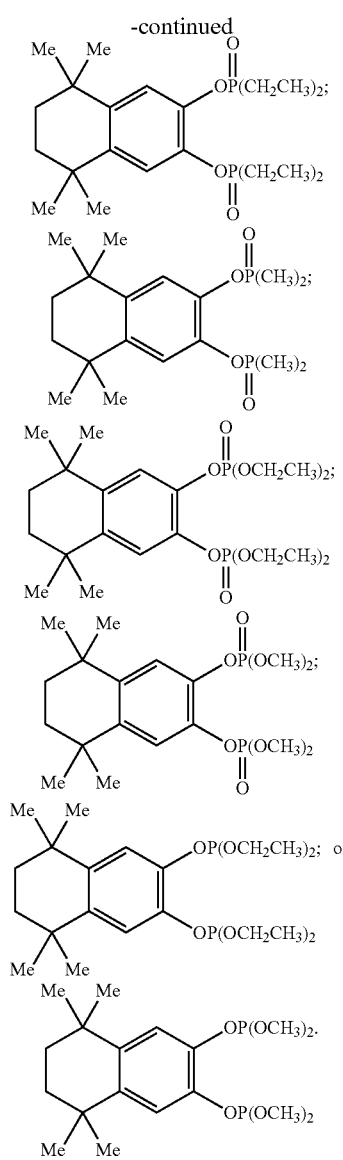

As further illustration of the compounds of Formula. II, the redox shuttle may include compounds represented as:

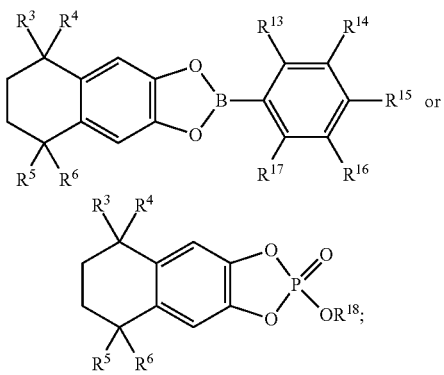

where $R^3$, $R^4$, $R^5$ and $R^6$ are independently F or alkyl; and $R^{13}$, $R^{14}$, $R^{15}$, $R^{16}$, $R^{17}$, and $R^{18}$ are independently H, F, Cl, Br, or alkyl. In some embodiments of the formulas, $R^3$, $R^4$, $R^5$ and $R^6$ are $CH_3$ or $CH_2CH_3$; and $R^{13}$, $R^{14}$, $R^{15}$, $R^{16}$, $R^{17}$, and $R^{18}$ are independently H, F, Cl, Br, $CH_3$, $CH_2CH_3$, $CH_2CH_2CH_3$, $CH(CH_3)_2CH_2F$, $CF_3$, $CH_2CH_3$ or $CH_2CF_2CF_3$.

By way of illustration only, and not intending to be limiting, the redox shuttles of Formula IV may include compounds such as:

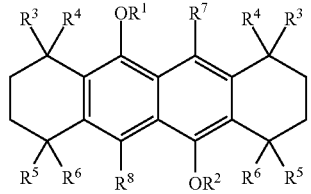

wherein: $R^3$, $R^4$, $R^5$ and $R^6$ are independently F or alkyl; and $R^1$ and $R^2$ are independently $CH_3$, $CH_2CH_3$, $CH_2CH_2CH_3$, $CH_2CH_2CH_2CH_3$, $CH(CH_3)_2$, $CH_2CH(CH_3)_2$, $CH_2CH_2OCH_3$, $CH_2CH_2OCH_2CH_2OCH_3$, $CH_2F$, $CH_2CF_3$, $CH_2CF_2CF_3$, $CH_2CF_2CF_2CF_3$, $CH_2CF_2CF_2H$, or $CH_2CF_2OCF_2H$, or $CH_2CF_2OCF_2CF_2OCF_2H$; and $R^7$ and $R^8$ are independently H, methyl, ethyl, methoxy, ethoxy, or trifluoromethoxy.

For example, the compounds of Formula IV may include, but are not limited to:

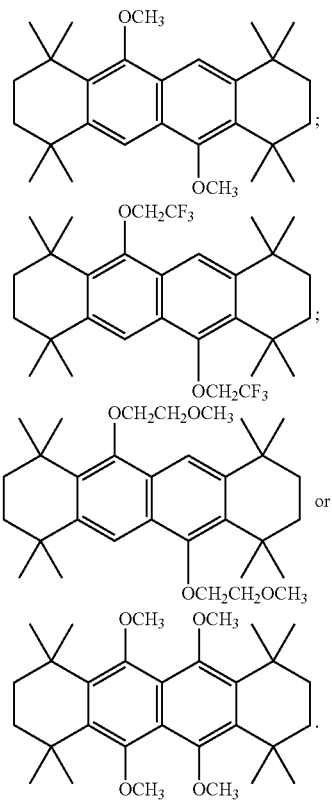

According to any of the described embodiments of the electrolyte, the concentration of the redox shuttle in the electrolyte ranges from about 0.0005 wt % and about 50 wt %. In some embodiments, the concentration is from about 0.05 wt % to about 25 wt %. In some other embodiments, the concentration is from about 0.05 wt % to about 10 wt %. In some embodiments, the concentration is from about 1 wt % to about 10 wt %.

A variety of alkali metal salts may be employed in the electrolytes for assisting in charge transfer through the electrolyte. Exemplary alkali metal salts include, but are not limited to lithium salts that are stable and soluble in the chosen charge-carrying media, such as LiBr, LiI, LiSCN, $LiBF_4$, $LiAlF_4$, $LiPF_6$, $LiAsF_6$, $LiClO_4$, $Li_2SO_4$, $LiB(Ph)_4$, $LiAlO_2$, $Li[N(FSO_2)_2]$, $Li[SO_3CH_3]$, $Li[BF_3(C_2F_5)]$, $Li[PF_3(CF_2CF_3)_3]$, $Li[B(C_2O_4)_2]$, $Li[B(C_2O_4)F_2]$, $Li[PF_4(C_2O_4)]$, $Li[PF_2(C_2O_4)_2]$, $Li[CF_3CO_2]$, $Li[C_2F_5CO_2]$, $Li[N(CF_3SO_2)_2]$, $Li[C(SO_2CF_3)_3]$, $Li[N(C_2F_5SO_2)_2]$, $Li[CF_3SO_3]$, $Li_2B_{12}X_{12-n'}H_{n'}$, $Li_2B_{10}X^2_{10-n''}H_{n''}$, $Li_2S_{x'''}$, $(LiS_{x'''}R^1)_{y'}$, $(LiSe_{x'''}R^1)_{y'}$, and lithium alkyl fluorophosphates; where $X^2$ is a halogen, n is an integer from 0 to 12, n' is an integer from 0 to 10, x" is an integer from 1 to 20, y is an integer from 1 to 3, and $R^1$ is H, alkyl, alkenyl, aryl, ether, F, $CF_3$, $COCF_3$, $SO_2CF_3$, or $SO_2F$. In some embodiments, the alkali metal salt is a mixture of any two or more such alkali metal salts. In one embodiment, the salt includes $Li[(C_2O_4)_2B]$, $Li(C_2O_4)BF_2$, $LiClO_4$, $LiBF_4$, $LiAsF_6$, $LiPF_6$, $LiCF_3SO_3$, $Li(CF_3SO_2)_2N$, $Li(CF_3SO_2)_3C$, $LiN(SO_2C_2F_5)_2$, or a lithium alkyl fluorophosphate. In another embodiment, the salt is other than $Li[B(C_2O_4)_2]$, $Li[BF_2(C_2O_4)]$, or $Li[PF_2(C_2O_4)]_2$, and the electrolyte further comprise about 0.001 to about 8 wt % of $Li[B(C_2O_4)_2]$, $Li[BF_2(C_2O_4)]$, or $Li[PF_2(C_2O_4)]_2$, or a mixture of any two or more thereof.

According to any of the described embodiments of the electrolyte, the polar aprotic solvent is a liquid or gel capable of solubilizing sufficient quantities of an alkali salt and a redox shuttle so that a suitable quantity of charge may be transported from the positive electrode to the negative electrode. Exemplary polar aprotic solvents can be used over a wide temperature range, e.g., from −30° C. to 70° C. without freezing or boiling, and are stable in the electrochemical window within which the cell electrodes and redox shuttles operate. Suitable solvents include ethylene carbonate, propylene carbonate, dimethyl carbonate; ethyl methyl carbonate; diethyl carbonate; methyl propyl carbonate; ethyl propyl carbonate; dipropyl carbonate; bis(trifluoroethyl)carbonate; bis(pentafluoropropyl)carbonate; trifluoroethyl methyl carbonate; pentafluoroethyl methyl carbonate; heptafluoropropyl methyl carbonate; perfluorobutyl methyl carbonate; trifluoroethyl ethyl carbonate; pentafluoroethyl ethyl carbonate; heptafluoropropyl ethyl carbonate; perfluorobutyl ethyl carbonate; fluorinated oligomers; dimethoxyethane; triglyme; dimethylvinylene carbonate; tetraethyleneglycol; dimethyl ether; polyethylene glycols; sulfones; and γ-butyrolactone. In one embodiment, the polar aprotic solvent includes ethylene carbonate, propylene carbonate, dimethyl carbonate, diethyl carbonate, ethyl methyl carbonate, dimethyl ether, or gamma butyrolactone. The solvent may include a mixture of any two or more of the above solvents.

In some embodiments, any of the electrolytes may also include an electrode stabilizing compound that can be reduced or polymerized on the surface of a negative electrode to form a passivation film on the surface of the negative electrode. In other embodiments, any of the electrolytes may also include an electrode stabilizing compound that can be reduced or polymerized on the surface of a positive electrode to form a passivation film on the surface of the positive electrode. In some embodiments, each electrode stabilizing compound is present in the electrolyte at a concentration of 0.001 wt % to 10 wt %.

In another aspect, an electrochemical device is provided including a cathode; an anode; and any of the electrolytes described above. In some embodiments, the electrochemical device is a lithium secondary battery; the cathode is a lithium metal oxide cathode; the anode is a carbon or lithium metal anode; and the anode and cathode are separated from each other by a porous separator. In some such embodiments, the cathode is a spinel, olivine, or carbon-coated olivine cathode; and the anode is a graphite or amorphous carbon. Illustrative electrochemical devices include, but are not limited to lithium ion batteries, flow batteries, supercapacitors, lithium batteries, lithium air battery and sodium batteries.

A variety of negative electrodes may be employed in the electrochemical devices. Representative negative electrodes include $Li_4Ti_5O_{12}$; the lithium alloy compositions described in U.S. Pat. Nos. 6,203,944; 6,255,017; 6,436,578; 6,664,004; and 6,699,336; U.S. Patent Application Publication Nos. 2003/0211390; 2004/013 1936; 2005/0031957; and 2006/046144; graphitic carbons e.g., those having a spacing between (002) crystallographic planes, $d_{002}$, of 3.45 Å>$d_{002}$>3.354 Å and existing in forms such as powders, flakes, fibers or spheres (e.g., mesocarbon microbeads (MCMB)),; other materials that will be familiar to those skilled in the art; and combinations thereof.

A variety of positive electrodes may be employed in the electrochemical devices. Representative cathode materials include, a spinel, a olivine, a carbon-coated olivine, $LiFePO_4$, $LiCoO_2$, $LiNiO_2$, $LiNi_{1-x}Co_yM^4_zO_2$, $LiMn_{0.5}Ni_{0.5}O_2$, $LiMn_{1/3}CO_{1/3}Ni_{1/3}O_2$, $LiMn_2O_4$, $LiFeO_2$, $LiM^4_{0.5}Mn_{1.5}O_4$, $Li_{1+x''}Ni_\alpha Mn_\beta Co_\gamma M^5_\delta O_{2-z}F_{z'''}$, $A_n B^1_2(M^2O_4)_3$ (Nasicon), or $V_2O_5$. The cathodic material may include a combination of any two or more such positive active materials. In those positive active materials, $M^4$ may be Al, Mg, Ti, B, Ga, Si, Mn, or Co; $M^5$ may be Mg, Zn, Al, Ga, B, Zr, or Ti; A is Li, Ag, Cu, Na, Mn, Fe, Co, Ni, Cu, or Zn; $B^1$ may be Ti, V, Cr, Fe, or Zr; $M^2$ is P, S, Si, W, or Mo; $0 \leq x' \leq 0.3$; $0 \leq y \leq 0.5$; $0 \leq z \leq 0.5$; $0 \leq m \leq 0.5$; $0 \leq n \leq 0.5$; $0 \leq x'' \leq 0.4$; $0 \leq \alpha \leq 1$; $0 \leq \beta \leq 1$; $0 \leq \gamma \leq 1$; $0 \leq \delta' \leq 0.4$; $0 \leq z' \leq 0.4$; $0 \leq z' \leq 0.5$; $0 \leq n' \leq 3$; and at least one of α, β, or γ is greater than 0. In some embodiments, the positive active material may be a spinel, a olivine, or a carbon-coated olivine, as described in U.S. Pat. No. 7,632,137. For example, the spinel may be a spinel manganese oxide of formula of $Li_{1+x}Mn_{2-z}M^4_yO_{4-m}X^1$, wherein $M^4$ is Al, Mg, Ti, B, Ga, Si, Ni, or Co; $X^1$ is S or F; $0 \leq x \leq 0.3$; $0 \leq y \leq 0.5$; $0 \leq z \leq 0.5$; $0 \leq m \leq 0.5$; and $0 \leq n \leq 0.5$. Alternatively, the positive active material may include an olivine of formula of $LiFe_{1-z}M^6_yPO_{4-m}X^1_n$, wherein $M^6$ is Al, Mg, Ti, B, Ga, Si, Ni, Mn or Co; $X^1$ is S or F; $0 \leq x \leq 0.3$; $0 \leq y \leq 0.5$; $0 \leq z \leq 0.5$; $0 \leq m \leq 0.5$; and $0 \leq n \leq 0.5$.

The negative or positive electrode may contain conductive carbon materials such as, but not limited to, porous active carbon materials which may include any such carbon material that is known for use in batteries. The material may include a high surface area carbon material and/or nanoparticulate carbon materials. For example, the high surface area carbon materials include, but are not limited to, microporous carbon, mesoporous carbon, mesoporous microbeads, graphite, expandable graphite, carbon black, carbon nanotubes, carbon nanofibers, graphene, crystalline graphite, amorphous graphite, hard carbon, soft carbon coal, and acetylene black. Commercial examples of carbon black include, but are not limited to, Super P, Black Pearl 2000, Denka Black, Vulcan XC72R, and Ketjen black.

The negative and positive electrode capacities may optionally be selected to provide an excess negative electrode capacity, which enables the shuttle to provide overcharge protection. From 10% to 20% excess negative electrode capacity is recommended. Lesser or greater excess negative electrode capacities may be employed if desired.

Anodic and cathodic materials of the electrochemical device are typically in contact with a current collector so that it may be effectively carry the current. The current collector may also be an adjacent material, such as the shell of a lithium-ion button cell. A variety of arrangements will work, so long as the negative and positive materials make suitable electrical contact with their associated current collectors. The current collector may be a conductive material. Illustrative current collectors include, but are not limited to, aluminum, nickel, platinum, palladium, gold, silver, copper, iron, stainless steel, rhodium, manganese, vanadium, titanium, tungsten, or aluminum carbon coated or any carbon-coated metal described above.

In some aspects, the electrolytes may include other additives to enhance the performance of the electrolyte when used in an electrochemical cell. For example, the electrolytes may also include an electrode stabilizing additive to protect the electrodes from degradation. Such electrode stabilizing additives are described by co-pending U.S. patent application Ser. Nos. 10/857,365 and 11/279,120. Such electrode stabilizing additives can be reduced or polymerized on the surface of a negative electrode to form a passivation film on the surface of the negative electrode. Likewise, electrolytes can include an electrode stabilizing additive that can be oxidized or polymerized on the surface of the positive electrode to form a passivation film on the surface of the positive electrode. In some embodiments, the electrolytes further include mixtures of the two types of electrode stabilizing additives. The additives are typically present at a concentration of from 0.001 wt % to 8 wt %.

In some embodiments, the electrode stabilizing additive is a substituted or unsubstituted linear, branched or cyclic hydrocarbon including at least one oxygen atom and at least one aryl, alkenyl or alkynyl group. Passivating films may be formed from a substituted aryl compound or a substituted or unsubstituted heteroaryl compound where the additive includes at least one oxygen atom. Alternatively, a combination of two additives may be used. In some embodiments, one additive is selective for forming a passivating film on the cathode to prevent leaching of metal ions and the other additive can be selective for passivating the anode surface to prevent or lessen the reduction of metal ions at the anode. Representative electrode stabilizing additives include 1,2-divinyl furoate, 1,3-butadiene carbonate, 1-vinylazetidin-2-one, 1-vinylaziridin-2-one, 1-vinylpiperidin-2-one, 1 vinylpyrrolidin-2-one, 2,4-divinyl-1,3-dioxane, 2 amino-3 vinylcyclohexanone, 2-amino-3-vinylcyclopropanone, 2 amino-4-vinylcyclobutanone, 2-amino-5-vinylcyclopentanone, 2-aryloxy-cyclopropanone, 2-vinyl-[1,2]oxazetidine, 2 vinylaminocyclohexanol, 2-vinylaminocyclopropanone, 2 vinyloxetane, 2-vinyloxy-cyclopropanone, 3-(N-vinylamino)cyclohexanone, 3,5-divinyl furoate, 3-vinylazetidin-2-one, 3 vinylaziridin 2 one, 3 vinylcyclobutanone, 3 vinylcyclopentanone, 3 vinyloxaziridine, 3 vinyloxetane, 3-vinylpyrrolidin-2-one, 4,4 divinyl-3 dioxolan 2-one, 4 vinyltetrahydropyran, 5-vinylpiperidin-3-one, allylglycidyl ether, butadiene monoxide, butyl vinyl ether, dihydropyran-3-one, divinyl butyl carbonate, divinyl carbonate, divinyl crotonate, divinyl ether, divinyl ethylene carbonate, divinyl ethylene silicate, divinyl ethylene sulfate, divinyl ethylene sulfite, divinyl methoxypyrazine, divinyl methylphosphate, divinyl propylene carbonate, ethyl phosphate, methoxy-o-terphenyl, methyl phosphate, oxetan-2-yl-vinylamine, oxiranylvinylamine, vinyl carbonate, vinyl crotonate, vinyl cyclopentanone, vinyl ethyl-2-furoate, vinyl ethylene carbonate, vinyl ethylene silicate, vinyl ethylene sulfate, vinyl ethylene sulfite, vinyl methacrylate, vinyl phosphate, vinyl-2-furoate, vinylcylopropanone, vinylethylene oxide, β-vinyl-γ-butyrolactone, or a mixture of any two or more thereof. In some embodiments the electrode stabilizing additive may be a cyclotriphosphazene that is substituted with F, alkyloxy, alkenyloxy, aryloxy, methoxy, allyloxy groups, or combinations thereof. For example, the additive may be a (divinyl)-(methoxy)(trifluoro)cyclotriphosphazene, (trivinyl)(difluoro)(methoxy)cyclotriphosphazene, (vinyl)(methoxy)(tetrafluoro)cyclotriphosphazene, (aryloxy)(tetrafluoro)(methoxy)-cyclotriphosphazene, (diaryloxy)(trifluoro)(methoxy)cyclotriphosphazene compounds, or a mixture of two or more such compounds. In some embodiments, the electrode stabilizing additive is vinyl ethylene carbonate, vinyl carbonate, or 1,2-diphenyl ether, or a mixture of any two or more such compounds.

Other representative electrode stabilizing additives may include compounds with phenyl, naphthyl, anthracenyl, pyrrolyl, oxazolyl, furanyl, indolyl, carbazolyl, imidazolyl, or thiophenyl groups. For example, electrode stabilizing additives may be aryloxpyrrole, aryloxy ethylene sulfate, aryloxy pyrazine, aryloxy-carbazole trivinylphosphate, aryloxy-ethyl-2-furoate, aryloxy-o-terphenyl, aryloxy-pyridazine, butyl-aryloxy-ether, divinyl diphenyl ether, (tetrahydro-furan-2-yl)-vinylamine, divinyl methoxybipyridine, methoxy-4-vinylbiphenyl, vinyl methoxy carbazole, vinyl methoxy piperidine, vinyl methoxypyrazine, vinyl methyl carbonate-allylanisole, vinyl pyridazine, 1-divinylimidazole, 3-vinyltetrahydrofuran, divinyl furan, divinyl methoxy furan, divinylpyrazine, vinyl methoxy imidazole, vinylmethoxy pyrrole, vinyl-tetrahydrofuran, 2,4-divinyl isooxazole, 3,4 divinyl-1-methylpyrrole, aryloxyoxetane, aryloxy-phenyl carbonate, aryloxy-piperidine, aryloxy-tetrahydrofuran, 2-aryl-cyclopropanone, 2-diaryloxy-furoate, 4-allylanisole, aryloxy-carbazole, aryloxy-2-furoate, aryloxy-crotonate, aryloxy-cyclobutane, aryloxy-cyclopentanone, aryloxy-cyclopropanone, aryloxy-cyclolophosphazene, aryloxy-ethylene silicate, aryloxy-ethylene sulfate, aryloxy-ethylene sulfite, aryloxy-imidazole, aryloxy-methacrylate, aryloxy-phosphate, aryloxy-pyrrole, aryloxyquinoline, diaryloxycyclotriphosphazene, diaryloxy ethylene carbonate, diaryloxy furan, diaryloxy methyl phosphate, diaryloxy-butyl carbonate, diaryloxy-crotonate, diaryloxy-diphenyl ether, diaryloxy-ethyl silicate, diaryloxy-ethylene silicate, diaryloxy-ethylene sulfate, diaryloxyethylene sulfite, diaryloxy-phenyl carbonate, diaryloxy-propylene carbonate, diphenyl carbonate, diphenyl diaryloxy silicate, diphenyl divinyl silicate, diphenyl ether, diphenyl silicate, divinyl methoxydiphenyl ether, divinyl phenyl carbonate, methoxycarbazole, or 2,4-dimethyl-6-hydroxy-pyrimidine, vinyl methoxyquinoline, pyridazine, vinyl pyridazine, quinoline, vinyl quinoline, pyridine, vinyl pyridine, indole, vinyl indole, triethanolamine, 1,3-dimethyl butadiene, butadiene, vinyl ethylene carbonate, vinyl carbonate, imidazole, vinyl imidazole, piperidine, vinyl piperidine, pyrimidine, vinyl pyrimidine, pyrazine, vinyl pyrazine, isoquinoline, vinyl isoquinoline, quinoxaline, vinyl quinoxaline, biphenyl, 1,2-diphenyl ether, 1,2-diphenylethane, o terphenyl, N-methylpyrrole, naphthalene, or a mixture of any two or more such compounds.

In other embodiments, electrode stabilizing additives include substituted or unsubstituted spirocyclic hydrocarbons containing at least one oxygen atom and at least one alkenyl or alkynyl group. For example, such stabilizing additives include those having Formula V:

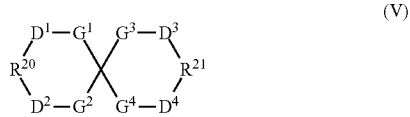 (V)

where: $D^1$, $D^2$, $D^3$, $D^4$, $G^1$, $G^2$, $G^3$, and $G^4$ are independently O or $CR^{22}R^{23}$; provided that $D^1$ is not O when $G^1$ is O, $D^2$ is not O when $G^2$ is O, $D^3$ is not O when $G^3$ is O, and $D^4$ is not O when $G^4$ is O; $R^{20}$ and $R^{21}$ are independently a divalent alkenyl or alkynyl group; and $R^{22}$ and $R^{23}$ at each occurrence are independently H, F, Cl, alkyl, alkenyl, or alkynyl group.

Representative examples of Formula V include, but are not limited to, 3,9 divinyl-2,4,8,10-tetraoxaspiro[5.5]undecane, 3,9-divinyl-2,4,8-trioxaspiro[5.5]undecane, 3,9-divinyl-2,4-dioxaspiro[5.5]undecane, 3,9-diethylidene-2,4,8,10-tetraoxaspiro[5.5]undecane, 3,9 diethylidene-2,4,8-trioxaspiro[5.5]undecane, 3,9-diethylidene-2,4-dioxaspiro[5.5]undecane, 3,9-dimethylene-2,4,8,10-tetraoxaspiro[5.5]undecane, 3,9-divinyl-1,5,7,11-tetraoxaspiro[5.5]undecane, 3,9 dimethylene-1,5,7,11-tetraoxaspiro[5.5]undecane, 3,9 diethylidene-1,5,7,11-tetraoxaspiro[5.5]undecane, or a mixture of any two or more such compounds. Furthermore, mixtures of any two or more electrode stabilizing additives may also be used in the electrolytes.

In some embodiments, the electrode stabilizing additive is an anion receptor. In some embodiments, the anion receptor is a Lewis acid. In other embodiments, the anion receptor is a borane, a boronate, a borate, a borole, or a mixture of any two or more such compounds. In some embodiments, the anion receptor is a compound of the Formula VI:

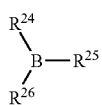 VI where, each $R^{24}$, $R^{25}$, and $R^{26}$ are independently halogen, alkyl, aryl, halogen-substituted alkyl, halogen-substituted aryl, or $OR^{24}$; or any two of $R^{24}$, $R^{25}$, and $R^{26}$, together with the atoms to which they are attached, form a heterocyclic ring having 5-9 members, and $R^{24}$ is at each occurrence independently alkyl, aryl, halogen-substituted alkyl, or halogen-substituted aryl.

In some embodiments, the anion receptors include, but are not limited to, tri(propyl)borate, tris(1,1,1,3,3,3-hexafluoropropan-2-yl)borate, tris(1,1,1,3,3,3-hexafluoro-2-phenyl-propan-2-yl)borate, tris(1,1,1,3,3,3-hexafluoro-2-(trifluoromethyl)propan-2-yl)borate, triphenyl borate, tris(4-fluorophenyl)borate, tris(2,4-difluorophenyl)borate, tris(2,3,5,6-tetrafluorophenyl)borate, tris(pentafluorophenyl)borate, tris(3-(trifluoromethyl)phenyl)borate, tris(3,5-bis(trifluoromethyl)phenyl)borate, tris(pentafluorophenyl)borane, or a mixture of any two or more thereof. Further suitable additives include 2-(2,4-difluorophenyl)-4-fluoro-1,3,2-benzodioxaborole, 2-(3-trifluoromethyl phenyl)-4-fluoro-1,3,2-benzodioxaborole, 2,5-bis(trifluoromethyl)phenyl-4-fluoro-1,3,2-benzodioxaborole, 2-(4-fluorophenyl)-tetrafluoro-1,3,2-benzodioxaborole, 2-(2,4-difluorophenyl)-tetrafluoro-1,3,2-benzodioxaborole, 2-(pentafluorophenyl)-tetrafluoro-1,3,2-benzodioxaborole, 2-(2-trifluoromethyl phenyl)-tetrafluoro-1,3,2-benzodioxaborole, 2,5-bis(trifluoromethyl phenyl)-tetrafluoro-1,3,2-benzodioxaborole, 2-phenyl-4,4,5,5-tetra(trifluoromethyl)-1,3,2-benzodioxaborolane, 2-(3,5-difluorophenyl-4,4,5,5-tetrakis(trifluoromethyl)-1,3,2-dioxaborolane, 2-(3,5-difluorophenyl-4,4,5,5-tetrakis(trifluoromethyl)-1,3,2-dioxaborolane, 2-pentafluorophenyl-4,4,5,5-tetrakis(trifluoromethyl)-1,3,2-dioxaborolane, bis(1,1,1,3,3,3-hexafluoroisopropyl)phenyl-boronate, bis(1,1,1,3,3,3-hexafluoroisopropyl)-3,5-difluorophenylboronate, bis(1,1,1,3,3,3-hexafluoroisopropyl)pentafluorophenylboronate, or a mixture of any two or more such compounds. In some embodiments, each anion receptor is present at a concentration from 0.001 wt % to 10 wt %.

In some other embodiments, the electrode stabilizing additive comprises pyridazine, vinyl pyridazine, quinoline, vinyl quinoline, pyridine, vinyl pyridine, indole, vinyl indole, triethanolamine, 1,3-dimethyl butadiene, butadiene, vinyl ethylene carbonate, vinyl carbonate, imidazole, vinyl imidazole, piperidine, vinyl piperidine, pyrimidine, vinyl pyrimidine, pyrazine, vinyl pyrazine, isoquinoline, vinyl isoquinoline, quinoxaline, vinyl quinoxaline, biphenyl, 1,2-diphenyl ether, 1,2-diphenylethane, o-terphenyl, N-methylpyrrole, naphthalene, 3,9-divinyl-2,4,8,10-tetraoxaspiro[5.5]undecane, 3,9-divinyl-2,4,8-trioxaspiro[5.5]undecane, 3,9-divinyl-2,4-dioxaspiro[5.5]undecane, 3,9-diethylidene-2,4,8,10-tetraoxaspiro[5.5]undecane, 3,9-diethylidene-2,4,8-trioxaspiro[5.5]undecane, 3,9-diethylidene-2,4-dioxaspiro[5.5]undecane, 3,9-dimethylene-2,4,8,10-tetraoxaspiro[5.5]undecane, 3,9-divinyl-1,5,7,11-tetraoxaspiro[5.5]undecane, 3,9-dimethylene-1,5,7,11-tetraoxaspiro[5.5]undecane, or 3,9-diethylidene-1,5,7,11-tetraoxaspiro[5.5]undecane. The electrode stabilizing additive may be present at any of the above concentrations. In some embodiments, the electrode stabilizing additive is present from about 0.001 wt % to about 8 wt %.

In some other embodiments, the electrolyte includes as an electrolyte additive, $Li_2B_{12}X_{12-n}H_n$, $Li_2B_{10}X_{10-n'}H_{n'}$, or a mixture of two or more of such compounds. Such electrolyte additives may be present from 0.001 wt % to 15 wt %. In such compounds, X is OH, $OCH_3$, F, Cl, Br, or I, n is an integer from 0 to 12, and n' is an integer from 0 to 10.

In some embodiments, the electrolyte further includes a gel. Such electrolytes include a polar aprotic solvent, as above; a lithium salt, as above; any of the above a redox shuttles; a crosslinking agent; monofunctional monomeric compound; and at least one radical reaction initiator. In some embodiments, the gel electrolyte can also include other electrode stabilization additives and other electrolyte additives. Suitable crosslinking agents may be represented by Formula VII:

$$R^{27}-CH=C(R^{28})-C(=O)-O-(CH_2-CH(X')-)_{n'''}-O-C(=O)-C(R^{29})=CH-R^{30}$$  VII where $R^{27}$, $R^{28}$, $R^{29}$, and $R^{30}$ are each independently hydrogen, a substituted or unsubstituted alkyl group having from 1 to 12 carbon atoms, or a substituted or unsubstituted alkenyl group having from 2 to 12 carbon atoms; and where X' is a hydrogen, methyl, or ethyl group, and n' is an integer from 1 to 15. Monofunctional monomeric compounds may be used for the control of the crosslinking density of the gel electrolyte. Suitable monofunctional monomeric compounds include those of Formula VIII:

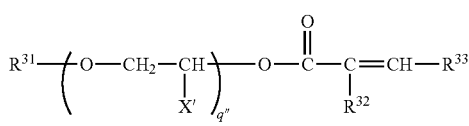

VIII where $R^{31}$ is an alkyl group having from 1 to 12 carbon atoms; $R^{32}$ and $R^{33}$ are each independently a hydrogen, a substituted or unsubstituted alkyl group having from 1 to 12 carbon atoms, or a substituted or unsubstituted alkenyl group having from 2 to 12 carbon atoms; X' is hydrogen, methyl or ethyl group; and q" is an integer from 1 to 20.

Crosslinking agents and monofunctional monomeric compounds provide a physical framework, or gel, after crosslinking to host the polar aprotic solvent. Variation of the amount of the crosslinking agent and monofunctional monomeric compound in the gel may impact the conductivity of the gel electrolyte, due to changes in viscosity. Lower viscosity gels are prepared with higher concentrations of monofunctional monomeric compound, as compared to the concentration of monofunctional monomeric compound used for higher viscosity gels. Without being bound by theory, higher viscosity gels may be expected to have lower electrochemical conductivity, while lower viscosity gels may be expected to have higher electrochemical conductivity. However, other electrochemical properties of the gel electrolyte, or an electrochemical cell prepared with the gel electrolyte, such as oxidation potential and reduction potential, are not expected to be impacted.

Polymerization of crosslinking agents and monofunctional monomeric compounds are known to those of skill in the art. For example, monofunctional monomeric compounds may be polymerized by thermal and photo initiation. Representative thermal initiators include, but are not limited to, an azo compound, a peroxide compound, bismaleimide, or a mixture of any two or more thereof. One example of an azo compound is azoisobutyronitrile. One example of a peroxide compound is benzoylperoxide. Representative photoinitiators include, but are not limited to, 1-hydroxyl-phenyl-ketone, benzophenone, 2-hydroxyl-2-methyl-1-phenyl-propanone, 2-hydroxyl-1-[4-(2-hydroxy)phenyl]-2-methyl-1-propanone, methylbenzoylformate, oxy-phenyl-acetic acid 2-[2-oxo-2-phenyl-acetoxy-ethoxy]-ethyl ester, oxy-phenyl-acetic 2-[2-hydroxy-ethoxy]-ethyl ester, α,α-dimethoxy-α-phenylacetophenone, 2-benzyl-2-(dimethylamino)-1-[4-(4-morpholinyl)phenyl]-1-propanone, diphenyl (2,4,6-trimethylthio)phenyl)-phosphine oxide, phosphine oxide, phenyl bis(2,4,6-trimethyl benzoyl), bis(η$^5$-2,4-cyclopentadien-1-yl)bis[2,6-difluoro-3-(1H-pyrrol-1-yl)phenyl]titanium, iodonium (4-methylphenyl)-[4-(2-methylpropyl)phenyl]-hexafluorophosphate, or a mixture of two or more thereof. In some instances the photoinitiator is a UV initiator.

In another aspect, a method of preparing the above electrolytes includes combining an alkali metal salt and a compound of Formula I, II, III, or IV in a polar aprotic solvent.

In another aspect, redox shuttle compounds are provided. According, a compound is provided that may be represented as Formula I, II, III, or IV:

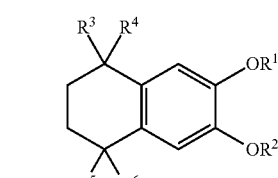

I

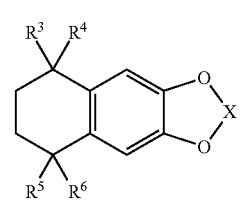

II

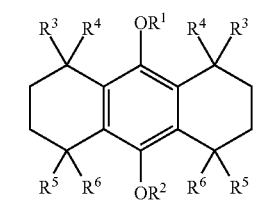

III

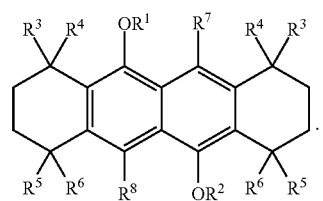

IV

In Formula I, II, III, and IV, $R^1$ and $R^2$ are independently alkyl, $P(O)R^9R^{10}$, $P(O)(OR^9)(OR^{10})$, or $P(OR^9)(OR^{10})$; $R^3$, $R^4$, $R^5$ and $R^6$ are independently F or alkyl; $R^7$, and $R^8$ are independently H, alkyl, or alkoxy; $R^9$ and $R^{10}$ are independently alkyl; X is alkylene, $BR^{11}$, or $P(O)OR^{12}$; $R^{11}$ is alkyl or aryl; and $R^{12}$ is alkyl, with the proviso that where the compound is of Formula I, at least one of $R^1$, $R^2$, $R^3$, $R^4$, $R^5$, and $R^6$ is other than methyl. In one embodiment, the compound is represented by Formula I. In another embodiment, the compound is represented by Formula II. In another embodiment, the compound is represented by Formula III. In another embodiment, the compound is represented by Formula IV.

In any of the above embodiments of the compound, $R^1$ and $R^2$ are independently $C_1$-$C_8$ alkyl, $P(O)R^9R^{10}$, $P(O)(OR^9)$ $(OR^{10})$, or $P(OR^9)(OR^{10})$; $R^3$, $R^4$, $R^5$ and $R^6$ are independently F or $C_1$-$C_2$ alkyl; $R^7$, and $R^8$ are independently H, $C_1$-$C_8$ alkyl, or $C_1$-$C_8$ alkoxy; $R^9$ and $R^{10}$ are independently $C_1$-$C_8$ alkyl; X is $C_1$-$C_4$ alkylene, $BR^{11}$, or $P(O)OR^{12}$; $R^{11}$ is $C_1$-$C_8$ alkyl or $C_6$-$C_{12}$ aryl; and $R^{12}$ is $C_1$-$C_8$ alkyl. In any of the above embodiments of the compound, $R^1$ and $R^2$ are independently $C_1$-$C_8$ alkyl or $C_1$-$C_8$ fluoroalkyl, $P(O)R^9R^{10}$, $P(O)(OR^9)(OR^{10})$, or $P(OR^9)(OR^{10})$; $R^3$, $R^4$, $R^5$ and $R^6$ are independently F $C_1$-$C_2$ alkyl, or $C_1$-$C_2$ fluoroalkyl; $R^7$, and $R^8$ are independently H, $C_1$-$C_8$ alkyl, $C_1$-$C_8$ fluoroalkyl, $C_1$-$C_8$ alkoxy, or $C_1$-$C_8$ fluoroalkoxy; $R^9$ and $R^{10}$ are independently $C_1$-$C_8$ alkyl or $C_1$-$C_8$ fluoroalkyl; X is $C_1$-$C_4$ alkylene, $BR^{11}$, or $P(O)OR^{12}$; $R^{11}$ is $C_1$-$C_8$ alkyl, $C_1$-$C_8$ fluoroalkyl, or substituted or unsubstituted phenyl; and $R^{12}$ is $C_1$-$C_8$ alkyl or $C_1$-$C_8$ fluoroalkyl.

According to one embodiment where the compound is represented by Formula I, $R^1$ and $R^2$ are $C_1$-$C_8$ alkyl or $C_1$-$C_8$ fluoroalkyl, $P(O)R^9R^{10}$, $P(O)(OR^9)(OR^{10})$, or $P(OR^9)$ $(OR^{10})$; $R^3$, $R^4$, $R^5$ and $R^6$ are independently F, $C_1$-$C_2$ alkyl, $C_1$-$C_2$ fluoroalkyl; and $R^9$ and $R^{10}$ are independently $C_1$-$C_8$ alkyl, with the proviso that where the compound is of Formula I, at least one of $R^1$, $R^2$, $R^3$, $R^4$, $R^5$, and $R^6$ is other than methyl. According to one embodiment where the compound is represented by Formula II, $R^1$ and $R^2$ are $C_1$-$C_8$ alkyl or $C_1$-$C_8$ fluoroalkyl, $P(O)R^9R^{10}$, $P(O)(OR^9)(OR^{10})$, or $P(OR^9)$ $(OR^{10})$; $R^3$, $R^4$, $R^5$ and $R^6$ are independently F, $C_1$-$C_2$ alkyl, $C_1$-$C_2$ fluoroalkyl; and $R^9$ and $R^{10}$ are independently $C_1$-$C_8$ alkyl; and X is $C_1$-$C_4$ alkylene, $BR^{11}$, or $P(O)OR^{12}$; $R^{11}$ is $C_1$-$C_8$ alkyl, $C_1$-$C_8$ fluoroalkyl, or substituted or unsubstituted phenyl; and $R^{12}$ is $C_1$-$C_8$ alkyl or $C_1$-$C_8$ fluoroalkyl.

In any of the above embodiments, $R^1$ and $R^2$ may be independently $CH_3$, $CH_2CH_3$, $CH_2CH_2CH_3$, $CH_2CH_2CH_2CH_3$, $CH(CH_3)_2$, $CH_2CH(CH_3)_2$, $CH_2CH_2OCH_3$, $CH_2CH_2OCH_2CH_2OCH_3$, $CH_2F$, $CH_2CF_3$, $CH_2CF_2CF_3$, $CH_2CF_2CF_2CF_3$, $CH_2CF_2CF_2H$, $CH_2CF_2OCF_2H$, $CH_2CH_2OCF_2CF_2OCF_2H$; $P(O)(OCH_3)_2$, $P(O)(OCH_2CH_3)_2$, $P(O)(OCH_3)_2$, or $P(O)(CH_2CH_3)_2$. In any of the above embodiments, X may be BPh, $CH_2$, $CH_2CH_2$, $CH_2CH_2CH_2$, $CH_2CH_2CH_2CH_2$, $P(O)OCH_3$, or $P(O)OCH_2CH_3$.

By way of illustration only, and not intending to be limiting, the compounds of Formula I and II may include:

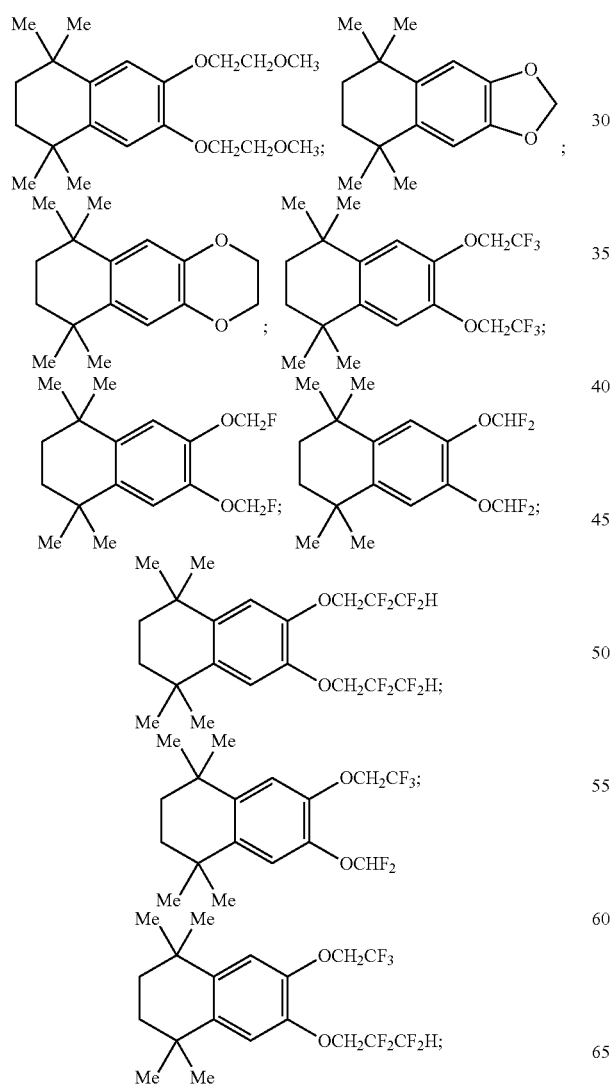

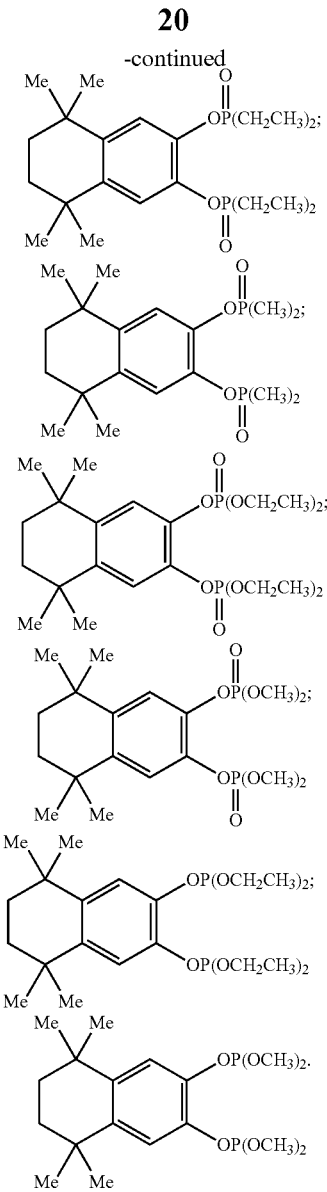

As further illustration of the compounds of Formula II, the compounds may be represented as:

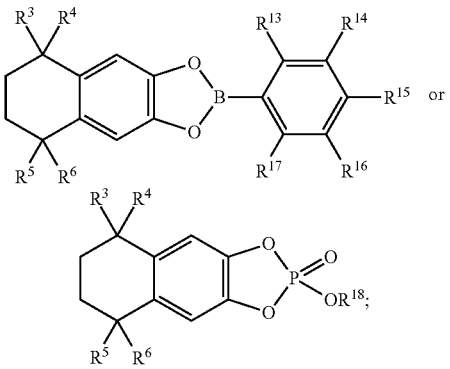

where $R^3$, $R^4$, $R^5$ and $R^6$ are independently F or alkyl; and $R^{13}$, $R^{14}$, $R^{15}$, $R^{16}$, $R^{17}$ and $R^{18}$ are independently H, F, Cl, Br, or alkyl. In some embodiments of the formulas, $R^3$, $R^4$, $R^5$ and $R^6$ are $CH_3$ or $CH_2CH_3$; and $R^{13}$, $R^{14}$, $R^{15}$, $R^{16}$, $R^{17}$, and $R^{18}$ are independently H, F, Cl, Br, $CH_3$, $CH_2CH_3$, $CH_2CH_2CH_3$, $CH(CH_3)_2CH_2F$, $CF_3$, $CH_2CF_3$, or $CH_2CF_2CF_3$.

By way of illustration only, and not intending to be limiting, the compounds of Formula IV may include compounds such as:

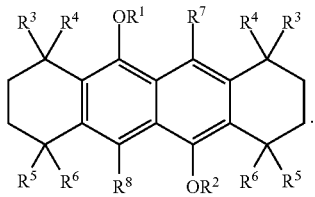

IV wherein: $R^3$, $R^4$, $R^5$ and $R^6$ are independently F or alkyl; and $R^1$ and $R^2$ are independently $CH_2CH_3$, $CH_2CH_2CH_3$, $CH_2CH_2CH_2CH_3$, $CH(CH_3)_2$, $CH_2CH(CH_3)_2$, $CH_2CH_2OCH_3$, $CH_2CH_2OCH_2CH_2OCH_3$, $CH_2F$, $CH_2CF_3$, $CH_2CF_2CF_3$, $CH_2CF_2CF_2CF_3$, $CH_2CF_2CF_2H$, or $CH_2CF_2OCF_2H$, or $CH_2CF_2OCF_2CF_2OCF_2H$; and $R^7$ and $R^8$ are independently H, methyl, ethyl, methoxy, ethoxy, or trifluoromethoxy.

For example, the compounds of Formula IV may include, but are not limited to:

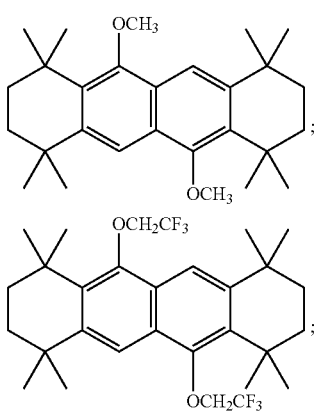

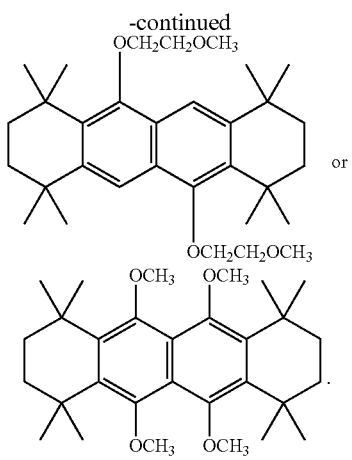

In another aspect, a process of preparing the compounds is provided. The method includes contacting a dihaloalkane with an aromatic compound having two ortho-substituted alkoxy groups in the presence of a Friedel-Crafts catalyst, followed by dealkylation of the alkoxy groups to produce a catechol, which in turn is followed by reaction of the catechol with an alkylating agent, boronating agent, or phosphating agent. The process may be illustrated as is shown in Scheme 1 with regard to the preparation of 1,1,4,4-tetramethyl-6,7-bis(2,2,2-trifluoroethoxy)-1,2,3,4-tetrahydronaphthalene.

Scheme 1:

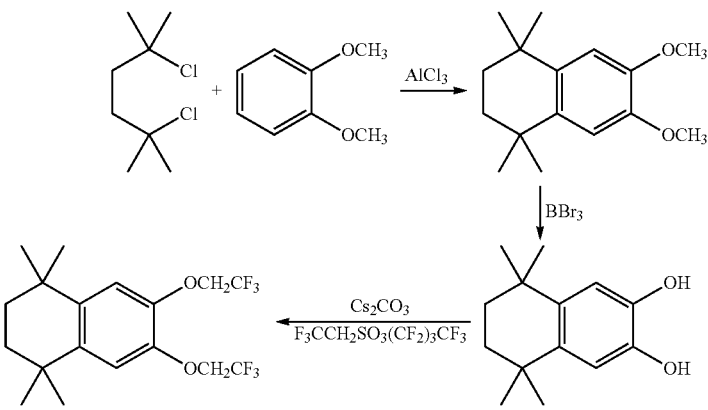

In such a process, the Friedel-Crafts catalyst may be aluminum chloride, and the reaction of the 2,5-dichloro-2,5-dimethylhexane with the 1,2-dimethoxybenzene provides the dimethoxy compound, 6,7-dimethoxy-1,1,4,4-tetramethyl-1,2,3,4-tetrahydronaphthalene. Reaction of the dimethoxy compound with tribromoborane, removes the alkyl groups from the alkoxy groups to produce a catechol compound (i.e. a benzene ring having 1,2-dihydroxy substitution), 5,5,8,8-tetramethyl-5,6,7,8-tetrahydronaphthalene-2,3-diol. The catechol is then reacted with an alkylating agent to produce the product. Other agents that may be used in place of the alkylating agent include those compounds which will provide boronated or phosphonated products. Other alkyl substitutions may be used as will be recognized by those of skill in the art to prepare the claimed compounds. Additionally, 1,2,-dialkoxybenzenes, other than 1,2-dimethoxybenzene may be used to directly prepare the desired products via a Friedel-Crafts alkylation with a dihaloalkane, such as 2,5-dichloro-2,5-dimethylhexane.

Illustrative compounds prepared by the process include, but are not limited to,

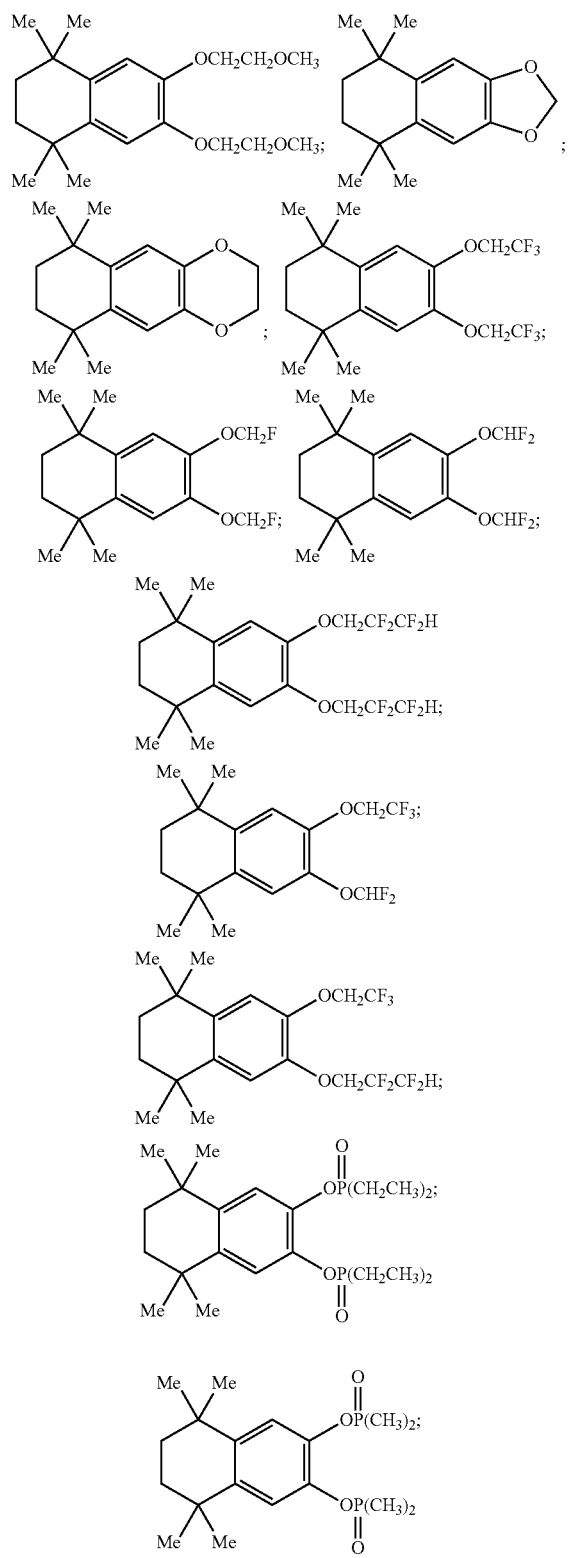

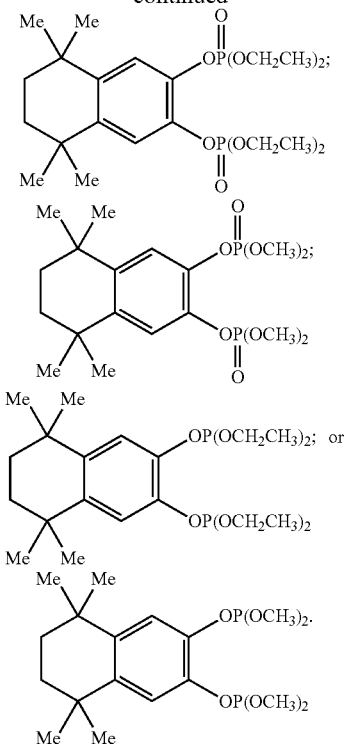

The present technology, thus generally described, will be understood more readily by reference to the following examples, which are provided by way of illustration and are not intended to be limiting.

EXAMPLES

Example 1

Synthesis of 1,2,3,4-tetrahydro-6,7-dimethoxy-1,1,4,4-tetramethylnaphthalene 2,5-dichloro-2,5-dimethylhexane (2.2 g, 12 mmol), 1,2-dimethoxybenzene (1.38 g, 10 mmol), anhydrous 1,2-dichloroethane (10 mL) and anhydrous AlCl₃ (200 mg) were combined in a 100 mL Schlenk flask under Ar. The mixture was heated at 60° C. for 6 h before quenching with ice water. The layers were then separated, and the aqueous layer extracted three times with CH₂Cl₂. The combined organic layers were washed with brine, dried over MgSO₄, filtered, and concentrated in vacuo. The remaining residue was purified by flash column chromatography (hexanes/Ethyl acetate=10:1) to afford the title compound (1.1 g, 35% yield). ¹H NMR (CDCl$_3$): 1.27 (s, 12H), 1.67 (s, 4H), 3.86 (s, 6H), 6.77 (s, 2H); $^{13}$C NMR (CDCl$_3$): 32.07, 34.22, 35.42, 56.01, 109.37, 137.23, 147.05.

Example 2

Synthesis of 5,6,7,8-tetrahydro-5,5,8,8-tetramethyl-2,3-naphthalenediol

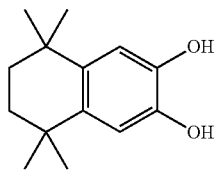 [SMILES: CC1(C)CCC(C)(C)c2cc(O)c(O)cc21]

1,2,3,4-tetrahydro-6,7-dimethoxy-1,1,4,4-tetramethylnaphthalene (Example 1, 0.7 g, 2.82 mmol) was dissolved in anhydrous CH$_2$Cl$_2$. At −78° C., BBr$_3$ (2.96 mL, 2.96 mmol, 1.0M in CH$_2$Cl$_2$) was slowly added. The reaction mixture was allowed to warm up to room temperature and stir for 30 minutes before being quenched with ice water. The layers were separated, and the aqueous layer extracted three times with CH$_2$Cl$_2$. The combined organic layers were washed with brine, dried over MgSO$_4$, filtered and concentrated in vacuo to provide the title compound. $^1$H NMR (CDCl$_3$): 1.22 (s, 12H), 1.64 (s, 4H), 4.98 (s, 2H, —OH), 6.78 (s, 2H). This compound was used in the next step without further purification.

Example 3

Synthesis of 1,2,3,4-tetrahydro-1,1,4,4-tetramethyl-6,7-bis-(2,2,2-trifluoroethoxy)naphthalene

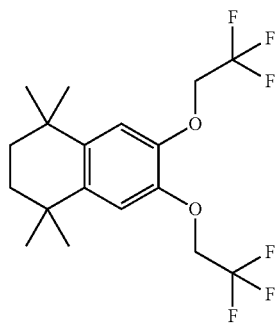 [SMILES: CC1(C)CCC(C)(C)c2cc(OCC(F)(F)F)c(OCC(F)(F)F)cc21]

To a Schlenk flask charged with 5,6,7,8-tetrahydro-5,5,8,8-tetramethyl-2,3-naphthalenediol (Example 2, 0.4 g, 1.71 mmol) dissolved in anhydrous DMF (20 mL), cesium carbonate (1.56 g, 4.78 mmol) was added. The color of the mixture turned from dark red to purple upon mixing. The mixture was heated at 60° C. for 2.5 h. The solution was then cooled to room temperature, and 2,2,2-trifluoroethylnonaflate (2 g, 5.13 mmol) was slowly added. After stirring overnight, the reaction was quenched with ice water. The layers were separated, and the aqueous layer was extracted three times with CH$_2$Cl$_2$. The combined organic layers were washed with brine, dried over MgSO$_4$, filtered and concentrated in vacuo. The residue was purified by flash column chromatography (hexanes) to afford the title compound. $^1$H NMR (CDCl$_3$): 1.24 (s, 12H), 1.66 (s, 4H), 4.35 (q, J=9 Hz, 4H, —OCH$_2$CF$_3$), 6.90 (s, 2H); $^{13}$C NMR (CDCl$_3$): 31.0, 33.8, 34.5, 67.4 (q, J=35 Hz, —OCH$_2$CF$_3$), 115.3, 124.3 (q, J=277 Hz, —OCH$_2$CF$_3$), 140.7, 145.5.

Example 4

A cell containing 1,2,3,4-tetrahydro-6,7-dimethoxy-1,1,4,4-tetramethylnaphthalene (5 mM; Example 1) in 1.2 M LiPF$_6$ in EC/EMC (3:7 wt ratio; EC is ethylene carbonate and EMC is ethylmethylcarbonate) was subjected to cyclic voltammetry (CV) using a three electrode system (Pt working Electrode, Li counter electrode and Li reference. The CV scans were done at different scan rates. FIG. 1 is a cyclic voltammogram (positive scan) of electrode) at different scan rates. The formal reduction potential was calculated as the average of the anodic and cathodic peak potentials. E=4.05 V. The compound exhibits high reversibility.

Example 5

Figure 2:
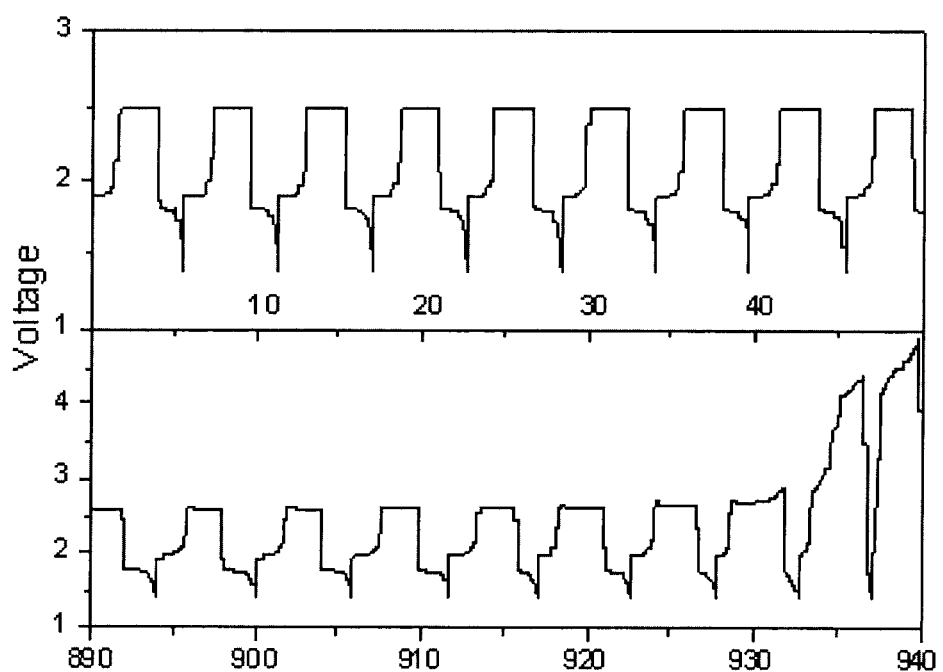
FIG. 2 is a voltage profile of a LTO/$LiFePO_4$ cell containing 0.4M 1,2,3,4-tetrahydro-6,7-dimethoxy-1,1,4,4-tetramethylnaphthalene in 1.2M $LiPF_6$ in EC/EMC (3:7) over the course of 0 to 940 hours, at a current rate of C/2, and 100% overcharge, according to the examples.

A cell was prepared with an anode of lithium titanium oxide (LTO) and a cathode of LiFePO$_4$. The cell contained a redox shuttle of 1,2,3,4-tetrahydro-6,7-dimethoxy-1,1,4,4-tetramethylnaphthalene (0.4 M), in 1.2M LiPF$_6$ in EC/EMC (3:7). The voltage profile for the cell was determined over the course of 0 to 940 hours, at a charging rate of C/2, and 100%. FIG. 2 is the voltage profile. The 1,2,3,4-tetrahydro-6,7-dimethoxy-1,1,4,4-tetramethylnaphthalene exhibits excellent overcharge protection performance in the carbonate-based electrolyte.

Example 6

Figure 3:
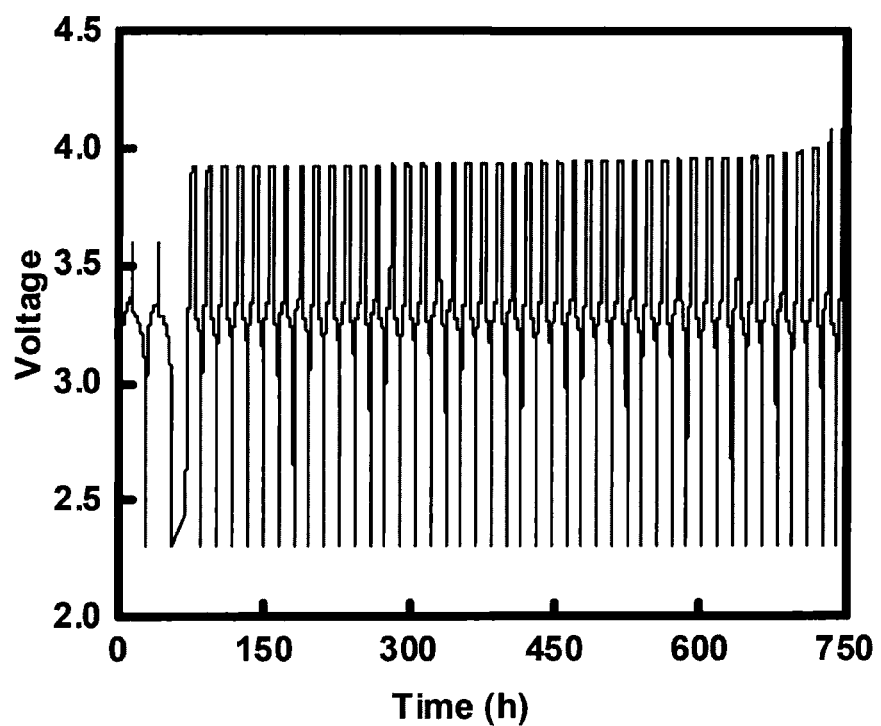
FIG. 3 is a voltage profile of a MCMB/$LiFePO_4$ cell containing 0.4M 1,2,3,4-tetrahydro-6,7-dimethoxy-1,1,4,4-tetramethylnaphthalene in 1.2M $LiPF_6$ in EC/EMC (3:7) over the course of 0 to 750 hours, at a current rate of C/5, and 100% overcharge, according to the examples.

A cell was prepared with an anode of mesocarbon microbeads (MCMB) and a cathode of LiFePO$_4$. The cell contained a redox shuttle of 1,2,3,4-tetrahydro-6,7-dimethoxy-1,1,4,4-tetramethylnaphthalene (0.4 M), in 1.2 M LiPF$_6$ in EC/EMC (3:7). The voltage profile was determined over the course of 0 to 750 hours, at a charging rate of C/5, and 100% overcharge. The first two cycles were charged and discharged in a voltage range between 3.6 V to 2.2 V. As illustrated in FIG. 3, the 1,2,3,4-tetrahydro-6,7-dimethoxy-1,1,4,4-tetramethylnaphthalene exhibits excellent overcharge protection performance in a carbonate-based electrolyte.

Example 7

Figure 4:
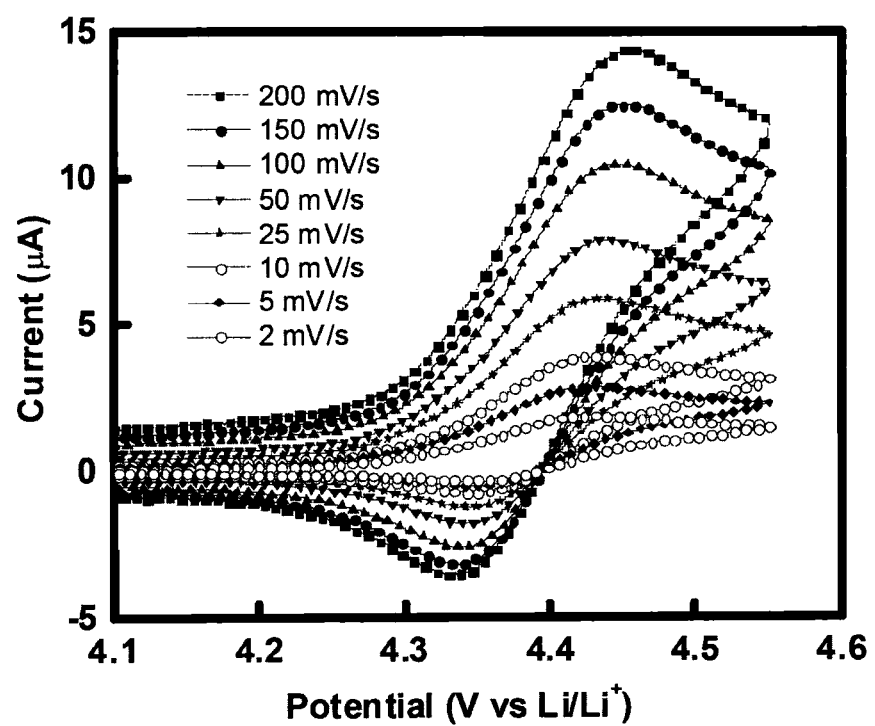
FIG. 4 is a cyclic voltammogram (positive scan) of 1,2,3,4-tetrahydro-1,1,4,4-tetramethyl-6,7-bis(2,2,2-trifluoroethoxy)naphthalene (5 mM) in 1.2 M $LiPF_6$ in EC/EMC (3:7) using a three electrode system (Pt working Electrode, Li counter electrode and Li reference electrode) at different scan rates, according to the examples.
Figure 5:
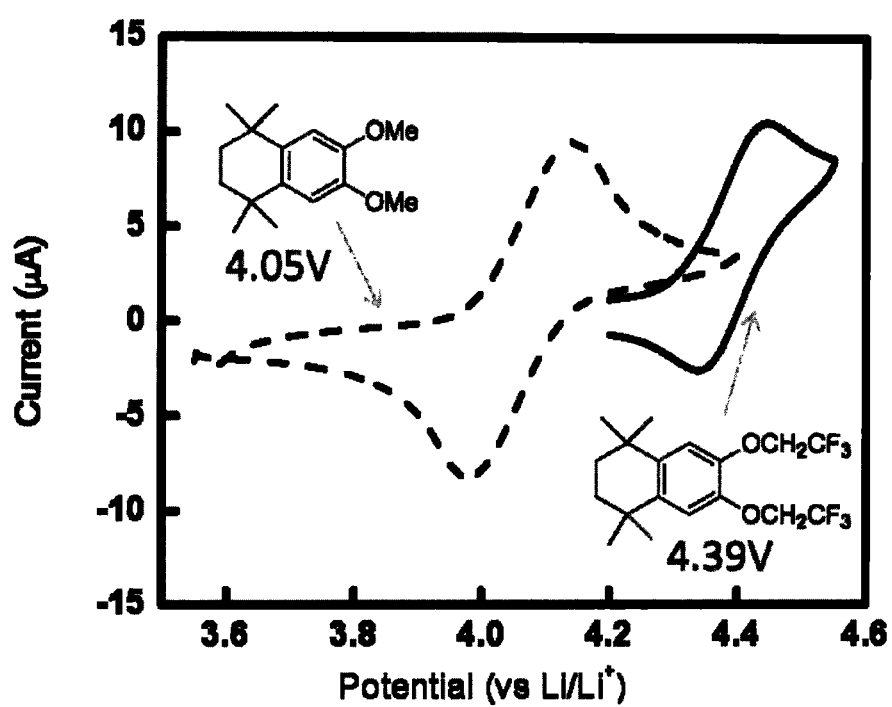
FIG. 5 is comparison of the cyclic voltammetric curves of 1,2,3,4-tetrahydro-1,1,4,4-tetramethyl-6,7-bis(2,2,2-trifluoroethoxy)naphthalene and 1,2,3,4-tetrahydro-6,7-dimethoxy-1,1,4,4-tetramethylnaphthalene, according to the examples.

A cell containing 1,2,3,4-tetrahydro-1,1,4,4-tetramethyl-6,7-bis(2,2,2-trifluoroethoxy)naphthalene (5 mM; Example 3) in 1.2 M LiPF$_6$ in EC/EMC (3:7 wt ratio; EC is ethylene carbonate and EMC is ethylmethylcarbonate) was subjected to cyclic voltammetry (CV) using a three electrode system (Pt working Electrode, Li counter electrode and Li reference. The CV scans were done at different scan rates. FIG. 4 is a cyclic voltammogram (positive scan) of electrode) at different scan rates. The formal reduction potential was calculated as the average of the anodic and cathodic peak potentials. E=4.39 V. The compound exhibits high reversibility. FIG. 5 is an overlay comparison of the cyclic voltammetric curves of 1,2,3,4-tetrahydro-1,1,4,4-tetramethyl-6,7-bis(2,2,2-trifluoroethoxy)naphthalene and 1,2,3,4-tetrahydro-6,7-dimethoxy-1,1,4,4-tetramethylnaphthalene.

Example 8

Figure 6:
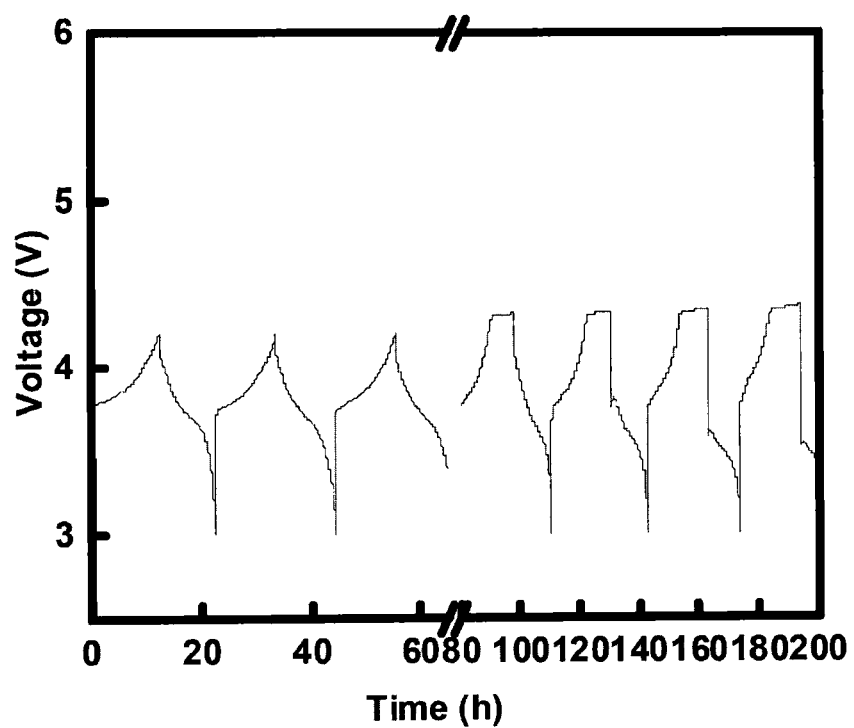
FIG. 6 is a voltage profile of LiNCM/Li cell containing 0.4M 1,2,3,4-tetrahydro-1,1,4,4-tetramethyl-6,7-bis(2,2,2-trifluoroethoxy)naphthalene in 1.2M $LiPF_6$ in EC/EMC (3:7) over the course of 0 to 200 hours at a current rate of C/10, and 100% overcharge, according to the examples.
Figure 7:
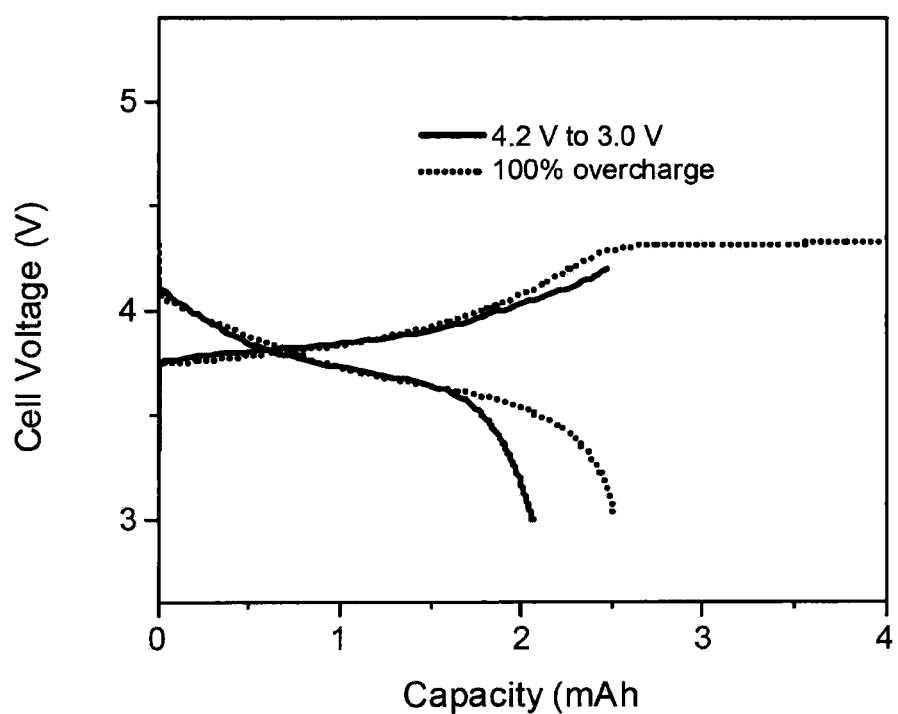
FIG. 7 is a capacity/voltage profiles of a LiNCM/Li cell containing 0.4M 1,2,3,4-tetrahydro-1,1,4,4-tetramethyl-6,7-bis(2,2,2-trifluoroethoxy)naphthalene in 1.2M $LiPF_6$ in 1.2M $LiPF_6$ in EC/EMC (3:7), during normal cycle condition (4.2 V to 3.0 V) and cycle with 100% overcharge at a current rate of C/10, according to the examples.

A cell was prepared with a cathode of Li Ni$_{1/3}$CO$_{1/3}$Mn$_{1/3}$O$_2$ (LiNCM), and an anode of Li. The cell contained a redox shuttle of 1,2,3,4-tetrahydro-1,1,4,4-tetramethyl-6,7-bis(2,2,2-trifluoroethoxy)naphthalene (0.4 M), in 1.2 M LiPF$_6$ in EC/EMC (3:7). The voltage profile was determined over the course of 0 to 200 hours, at a charging rate of C/10, and 100% overcharge. The first three cycles were charged and discharged between 4.1 V to 3.0V. As illustrated in FIG. 6, the 1,2,3,4-tetrahydro-6,7-dimethoxy-1,1,4,4-tetramethylnaphthalene exhibits excellent overcharge protection performance in a carbonate-based electrolyte. FIG. 7 is a capacity/voltage profile of the same cell.

Equivalents

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent compositions, apparatuses, and methods within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

While certain embodiments have been illustrated and described, it should be understood that changes and modifications can be made therein in accordance with ordinary skill in the art without departing from the technology in its broader aspects as defined in the following claims.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

What is claimed is:
1. An electrolyte comprising:
an alkali metal salt;
an aprotic solvent; and
a redox shuttle additive comprising a compound represented by Formula I, II, III, or IV:

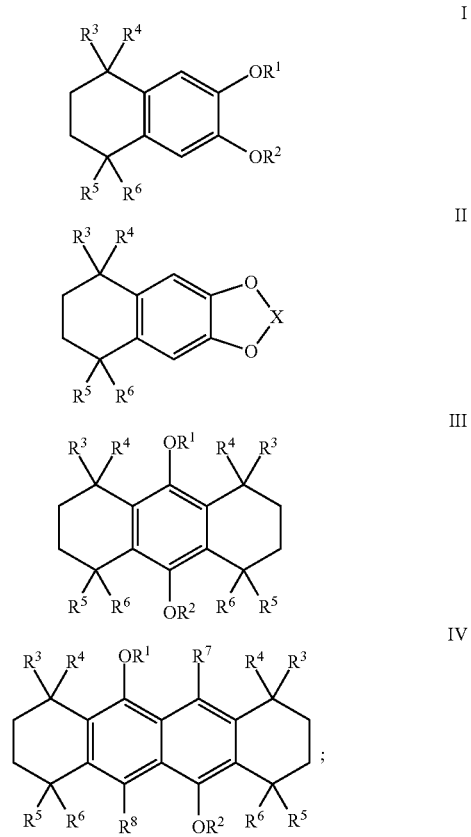

wherein:
R$^1$ and R$^2$ are independently substituted or unsubstituted C$_1$-C$_{20}$ alkyl, substituted or unsubstituted C$_1$-C$_{20}$ fluoroalkyl, substituted or unsubstituted C$_1$-C$_{20}$ ether, P(O)R$^9$R$^{10}$, P(O)(OR$^9$)(OR$^{10}$), or P(OR$^9$)(OR$^{10}$);
R$^3$, R$^4$, R$^5$ and R$^6$ are independently F, substituted or unsubstituted C$_1$-C$_{20}$ fluoroalkyl, or substituted or unsubstituted C$_1$-C$_{20}$ alkyl;

R[7], and R[8] are independently H, substituted or unsubstituted $C_1$-$C_{20}$ alkyl, substituted or unsubstituted $C_1$-$C_{20}$ fluoroalkyl, or substituted or unsubstituted $C_1$-$C_{20}$ alkoxy;

R[9] and R[10] are independently substituted or unsubstituted $C_1$-$C_{20}$ alkyl or substituted or unsubstituted $C_1$-$C_{20}$ fluoroalkyl,;

X is alkylene, BR[11], or P(O)OR[12];

R[11] is substituted or unsubstituted $C_1$-$C_{20}$ alkyl, substituted or unsubstituted $C_1$-$C_{20}$ fluoroalkyl, or substituted or unsubstituted $C_1$-$C_{12}$ aryl; and R[12] is substituted or unsubstituted $C_1$-$C_{20}$ alkyl, or substituted or unsubstituted $C_1$-$C_{20}$ fluoroalkyl.

2. The electrolyte of claim 1, wherein R[1] and R[2] are independently substituted or unsubstituted $C_1$-$C_8$ alkyl, P(O)R[9]R[10], P(O)(OR[9])(OR[10]), or P(OR[9])(OR[10]); R[3], R[4], R[5] and R[6] are independently F or substituted or unsubstituted $C_1$-$C_2$ alkyl; R[7], and R[8] are independently H, substituted or unsubstituted $C_1$-$C_8$ alkyl, or substituted or unsubstituted $C_1$-$C_8$ alkoxy; R[9] and R[10] are independently substituted or unsubstituted $C_1$-$C_8$ alkyl; X is substituted or unsubstituted $C_1$-$C_4$ alkylene, BR[11], or P(O)OR[12]; R[11] is substituted or unsubstituted $C_1$-$C_8$ alkyl or substituted or unsubstituted $C_6$-$C_{12}$ aryl; and R[12] is substituted or unsubstituted $C_1$-$C_8$ alkyl.

3. The electrolyte of claim 1, wherein R[1] and R[2] are independently substituted or unsubstituted $C_1$-$C_8$ alkyl or substituted or unsubstituted $C_1$-$C_8$ fluoroalkyl, P(O)R[9]R[10], P(O)(OR[9])(OR[10]), or P(OR[9])(OR[10]); R[3], R[4], R[5] and R[6] are independently F, substituted or unsubstituted $C_1$-$C_2$ alkyl, or substituted or unsubstituted $C_1$-$C_2$ fluoroalkyl; R[7], and R[8] are independently H, substituted or unsubstituted $C_1$-$C_8$ alkyl, substituted or unsubstituted $C_1$-$C_8$ fluoroalkyl, substituted or unsubstituted $C_1$-$C_8$ alkoxy, or substituted or unsubstituted $C_1$-$C_8$ fluoroalkoxy; R[9] and R[10] are independently substituted or unsubstituted $C_1$-$C_8$ alkyl or substituted or unsubstituted $C_1$-$C_8$ fluoroalkyl; X is substituted or unsubstituted $C_1$-$C_4$ alkylene, BR[11], or P(O)OR[12]; R[11] is substituted or unsubstituted $C_1$-$C_8$ alkyl, substituted or unsubstituted $C_1$-$C_8$ fluoroalkyl, or substituted or unsubstituted phenyl; and R[12] is substituted or unsubstituted $C_1$-$C_8$ alkyl or substituted or unsubstituted $C_1$-$C_8$ fluoroalkyl.

4. The electrolyte of claim 1, wherein the redox shuttle comprises a compound represented by Formula I and R[1] and R[2] are substituted or unsubstituted $C_1$-$C_8$ alkyl or substituted or unsubstituted $C_1$-$C_8$ fluoroalkyl, P(O)R[9]R[10], P(O)(OR[9])(OR[10]), or P(OR[9])(OR[10]); R[3], R[4], R[5] and R[6] are independently F, substituted or unsubstituted $C_1$-$C_2$ alkyl, substituted or unsubstituted $C_1$-$C_2$ fluoroalkyl; and R[9] and R[10] are independently substituted or unsubstituted $C_1$-$C_8$ alkyl.

5. The electrolyte of claim 1, wherein the redox shuttle comprises a compound represented by Formula II and R[1] and R[2] are substituted or unsubstituted $C_1$-$C_8$ alkyl or substituted or unsubstituted $C_1$-$C_8$ fluoroalkyl, P(O)R[9]R[10], P(O)(OR[9])(OR[10]), or P(OR[9])(OR[10]); R[3], R[4], R[5] and R[6] are independently F, substituted or unsubstituted $C_1$-$C_2$ alkyl, substituted or unsubstituted $C_1$-$C_2$ fluoroalkyl; and R[9] and R[10] are independently substituted or unsubstituted $C_1$-$C_8$ alkyl; and X is substituted or unsubstituted $C_1$-$C_4$ alkylene, BR[11], or P(O)OR[12]; R[11] is substituted or unsubstituted $C_1$-$C_8$ alkyl, substituted or unsubstituted $C_1$-$C_8$ fluoroalkyl, or substituted or unsubstituted phenyl; and R[12] is $C_1$-$C_8$ alkyl or $C_1$-$C_8$ fluoroalkyl.

6. The electrolyte claim 1, wherein R[1] and R[2] are independently $CH_3$, $CH_2CH_3$, $CH_2CH_2CH_3$, $CH_2CH_2CH_2CH_3$, $CH(CH_3)_2$, $CH_2CH(CH_3)_2$, $CH_2CH_2OCH_3$, $CH_2CH_2OCH_2CH_2OCH_3$, $CH_2F$, $CH_2CF_3$, $CH_2CF_2CF_3$, $CH_2CF_2CF_2CF_3$, $CH_2CF_2CF_2H$, $CH_2CF_2OCF_2H$, $CH_2CF_2OCF_2CF_2OCF_2H$; $P(O)(OCH_3)_2$, $P(O)(OCH_2CH_3)_2$, $P(O)(CH_3)_2$, or $P(O)(CH_2CH_3)_2$.

7. The electrolyte claim 1, wherein X is BPh, $CH_2$, $CH_2CH_2$, $CH_2CH_2CH_2$, $CH_2CH_2CH_2CH_2$, $P(O)OCH_3$, or $P(O)OCH_2CH_3$.

8. The electrolyte of claim 1, wherein the redox shuttle comprises:

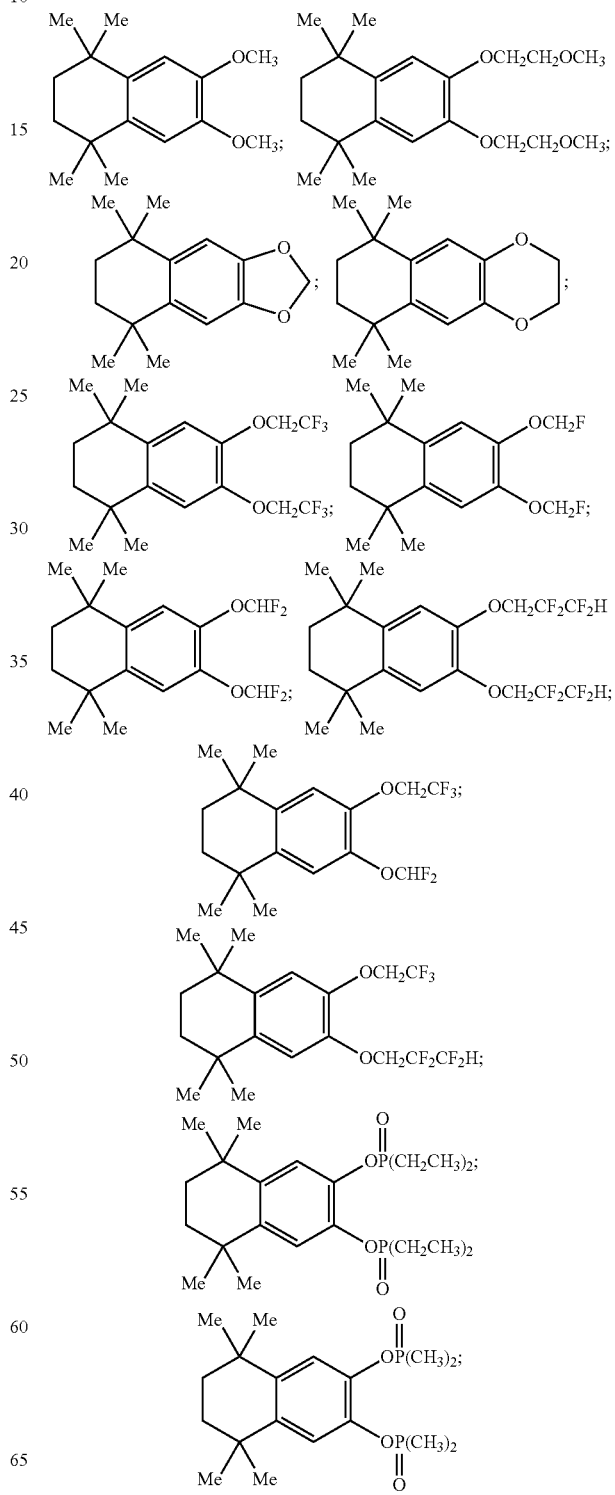

-continued

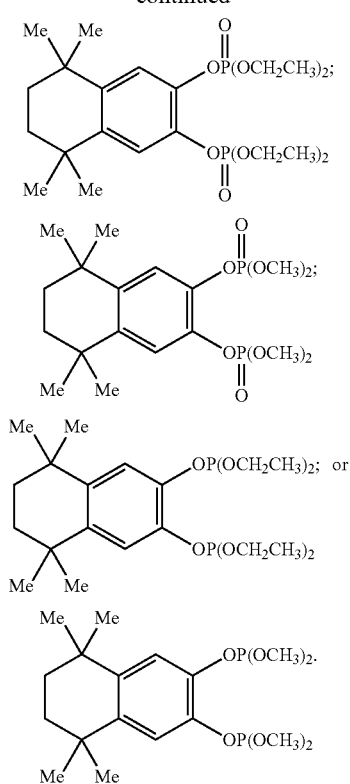

9. The electrolyte of claim 1, wherein the redox shuttle comprises:

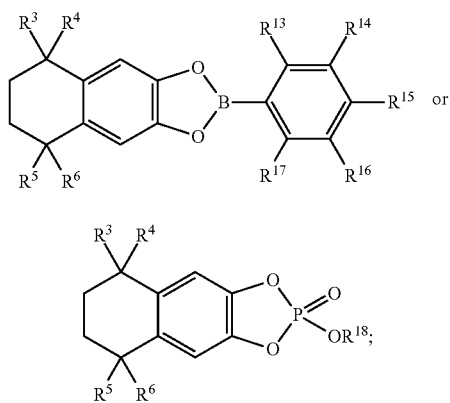

wherein:
R³, R⁴, R⁵ and R⁶ are independently F or substituted or unsubstituted alkyl; and R¹³, R¹⁴, R¹⁵, R¹⁶, R¹⁷, and R¹⁸ are independently H, F, Cl, Br, or substituted or unsubstituted $C_1$-$C_{20}$ alkyl.

10. The electrolyte of claim 9, wherein R³, R⁴, R⁵ and R⁶ are $CH_3$ or $CH_2CH_3$; and R¹³, R¹⁴, R¹⁵, R¹⁶, R¹⁷, and R¹⁸ are independently H, F, Cl, Br, $CH_3$, $CH_2CH_3$, $CH_2CH_2CH_3$, $CH(CH_3)_2CH_2F$, $CF_3$, $CH_2CF_3$, or $CH_2CF_2CF_3$.

11. The electrolyte of claim 1, wherein the redox shuttle comprises a compound of Formula IV:

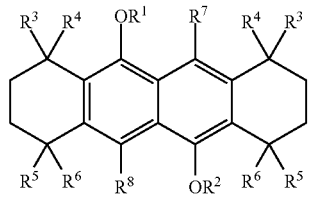

wherein: R³, R⁴, R⁵ and R⁶ are independently F or substituted or unsubstituted $C_1$-$C_{20}$ alkyl; and R¹ and R² are independently $CH_3$, $CH_2CH_3$, $CH_2CH_2CH_3$, $CH_2CH_2CH_2CH_3$, $CH(CH_3)_2$, $CH_2CH(CH_3)_2$, $CH_2CH_2OCH_3$, $CH_2CH_2OCH_2CH_2OCH_3$, $CH_2F$, $CH_2CF_3$, $CH_2CF_2CF_3$, $CH_2CF_2CF_2CF_3$, $CH_2CF_2CF_2H$, or $CH_2CF_2OCF_2H$, or $CH_2CF_2OCF_2CF_2OCF_2H$; and R⁷ and R⁸ are independently H, methyl, ethyl, methoxy, ethoxy, or trifluoromethoxy.

12. The electrolyte of claim 1 wherein the redox shuttle comprises:

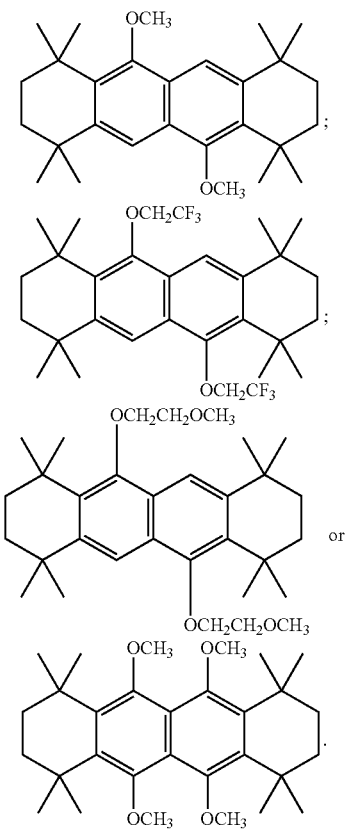

13. The electrolyte of claim 1, wherein the redox shuttle is present in the electrolyte from about 0.05 wt % to about 50 wt %, based upon the weight of the redox shuttle and the aprotic solvent.

14. The electrolyte of claim 1, wherein the alkali metal salt is a lithium salt.

15. The electrolyte of claim 1, wherein the lithium salt comprises LiBr, LiI, LiSCN, LiBF₄, LiAlF₄, LiPF₆, LiAsF₆, LiClO₄, Li₂SO₄, LiB(Ph)₄, LiAlO₂, Li[N(FSO₂)₂], Li[SO$_3$CH$_3$], Li[BF$_3$(C$_2$F$_5$)], Li[PF$_3$(CF$_2$CF$_3$)$_3$], Li[B(C$_2$O$_4$)$_2$], Li[B(C$_2$O$_4$)F$_2$], Li[PF$_4$(C$_2$O$_4$)], Li[PF$_2$(C$_2$O$_4$)$_2$], Li[CF$_3$CO$_2$], Li[C$_2$F$_5$CO$_2$], Li[N(CF$_3$SO$_2$)$_2$], Li[C(SO$_2$CF$_3$)$_3$], Li[N(C$_2$F$_5$SO$_2$)$_2$], Li[CF$_3$SO$_3$], Li$_2$B$_{12}$X$^2_{12-n}$H$_n$, Li$_2$B$_{10}$X$^2_{10-n'}$H$_{n'}$, Li$_2$S$_{x''}$, (LiS$_{x''}$R$^1$)$_y$, (LiSe$_{x''}$R$^1$)$_y$, and lithium alkyl fluorophosphates; where X$^2$ is a halogen, n is an integer from 0 to 12, n' is an integer from 0 to 10, x" is an integer from 1 to 20, y is an integer from 1 to 3, and R$^1$ is H, substituted or unsubstituted C$_1$-C$_{20}$ alkyl, substituted or unsubstituted C$_1$-C$_{20}$ alkenyl, substituted or unsubstituted C$_1$-C$_{12}$ aryl, substituted or unsubstituted C$_1$-C$_{20}$ ether, F, CF$_3$, COCF$_3$, SO$_2$CF$_3$, or SO$_2$F.

16. The electrolyte of claim 1, wherein the lithium salt comprises Li[(C$_2$O$_4$)$_2$B], Li(C$_2$O$_4$)BF$_2$, LiClO$_4$, LiBF$_4$, LiAsF$_6$, LiPF$_6$, LiCF$_3$SO$_3$, Li(CF$_3$SO$_2$)$_2$N, Li(CF$_3$SO$_2$)$_3$C, LiN(SO$_2$C$_2$F$_5$)$_2$, or a lithium alkyl fluorophosphate.

17. The electrolyte of claim 1, wherein the aprotic solvent comprises ethylene carbonate, propylene carbonate, dimethyl carbonate, diethyl carbonate, ethyl methyl carbonate, dimethyl ether, or gamma butyrolactone.

18. A lithium ion battery comprising a cathode, an anode, and the electrolyte according to claim 1.

* * * * *